US009393241B2

(12) United States Patent
Cohen et al.

(10) Patent No.: US 9,393,241 B2
(45) Date of Patent: *Jul. 19, 2016

(54) COMPOSITIONS FOR TREATING CMT AND RELATED DISORDERS

(71) Applicant: PHARNEXT, Issy les Moulineaux (FR)

(72) Inventors: Daniel Cohen, Le Vesinet (FR); Serguei Nabirochkin, Chatenay-Malabry (FR); Ilya Chumakov, Vaux le Penil (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/187,841

(22) Filed: Feb. 24, 2014

(65) Prior Publication Data

US 2014/0178463 A1 Jun. 26, 2014

Related U.S. Application Data

(63) Continuation-in-part of application No. 13/375,288, filed as application No. PCT/EP2010/057438 on May 28, 2010.

(30) Foreign Application Priority Data

Jun. 2, 2009 (EP) ..................... 09305506

(51) Int. Cl.
| | | |
|---|---|---|
| *A61K 31/485* | (2006.01) | |
| *A61K 31/047* | (2006.01) | |
| *A61K 31/197* | (2006.01) | |
| *A61K 31/436* | (2006.01) | |
| *A61K 31/192* | (2006.01) | |
| *A61K 31/4164* | (2006.01) | |
| *A61K 31/4178* | (2006.01) | |
| *A61K 31/567* | (2006.01) | |

(52) U.S. Cl.
CPC ............. *A61K 31/485* (2013.01); *A61K 31/047* (2013.01); *A61K 31/192* (2013.01); *A61K 31/197* (2013.01); *A61K 31/4164* (2013.01); *A61K 31/4178* (2013.01); *A61K 31/436* (2013.01); *A61K 31/567* (2013.01)

(58) Field of Classification Search
CPC .. A61K 31/485; A61K 31/047; A61K 31/197
See application file for complete search history.

(56) References Cited

U.S. PATENT DOCUMENTS

| | | | |
|---|---|---|---|
| 8,716,269 | B2 | 5/2014 | Cohen et al. |
| 8,992,891 | B2 | 3/2015 | Cohen et al. |
| 2003/0069213 | A1 | 4/2003 | Ii et al. |
| 2005/0038062 | A1 | 2/2005 | Burns et al. |
| 2005/0187290 | A1 | 8/2005 | Fontes et al. |
| 2007/0099947 | A1 | 5/2007 | Dean et al. |
| 2007/0110801 | A1 | 5/2007 | Perovitch et al. |
| 2007/0299098 | A1* | 12/2007 | Tanabe ........................ 514/282 |
| 2008/0206332 | A1* | 8/2008 | Kidney et al. ............... 424/468 |
| 2008/0255062 | A1 | 10/2008 | Fernyhough et al. |
| 2010/0310641 | A1 | 12/2010 | Cohen et al. |
| 2012/0040940 | A1 | 2/2012 | Cohen et al. |
| 2012/0088744 | A1 | 4/2012 | Cohen et al. |
| 2012/0270836 | A1 | 10/2012 | Cohen et al. |
| 2013/0085122 | A1 | 4/2013 | Cohen et al. |
| 2013/0090307 | A1 | 4/2013 | Cohen et al. |
| 2015/0157626 | A1 | 6/2015 | Cohen et al. |
| 2016/0113867 | A1 | 4/2016 | Cohen et al. |

FOREIGN PATENT DOCUMENTS

| | | |
|---|---|---|
| DE | 102006016990 A1 | 10/2007 |
| EP | 0778023 | 6/1997 |
| WO | WO 0020024 A2 | 4/2000 |
| WO | WO 03077867 A2 | 9/2003 |
| WO | WO 2004/006911 | 1/2004 |
| WO | WO 2004019938 A1 | 3/2004 |
| WO | WO 2004103263 A2 | 12/2004 |
| WO | WO 2005032555 A2 | 4/2005 |
| WO | WO 2005053612 A2 | 6/2005 |
| WO | WO 2006/117573 | 11/2006 |
| WO | WO 2007134077 A2 | 11/2007 |
| WO | WO 2007134136 A2 | 11/2007 |
| WO | WO 2009068668 A1 | 6/2009 |
| WO | WO 2009/153291 | 12/2009 |
| WO | WO 2011/054759 | 5/2011 |
| WO | WO 2012/117076 | 9/2012 |

OTHER PUBLICATIONS

Slavik, J. et al. "In Vitro Correlates of in Vivo Rapamycin Therapy in Patients with Multiple Sclerosis" *Clinical Immunology*, Jan. 1, 2006, p. S113, vol. 119.
Pomara, N. et al. "Mifepristone (RU 486) for Alzheimer's disease" *Neurology*, May 1, 2002, p. 1436, vol. 58, No. 9.
Gallagher, P. et al. "Persistent effects of mifepristone (RU-486) on cortisol levels in bipolar disorder and schizophrenia" *Journal of Psychiatric Research*, Oct. 1, 2008, pp. 1037-1041 vol. 42, No. 12.
Zu Horste, G. M. et al. "Myelin disorders: Causes and Perspectives of Charcot-Marie-Tooth Neuropathy" *Journal of Molecular Neuroscience*, Jan. 1, 2006, pp. 77-88, vol. 28, No. 1.
Herrmann, D. N. et al. "Experimental Therapeutics in Hereditary Neuropathies: The Past, the Present and the Future" *Neurotherapeutics*, Jan. 1, 2008, pp. 507-515, vol. 5, No. 4.
Gironi, M. et al. "A pilot trial of low-dose naltrexone in primary progressive multiple sclerosis" *Multiple Sclerosis*, Sep. 1, 2008, pp. 1076-1083, vol. 14, No. 8.
Cintas, P. et al. "Drug therapy for symptomatic relief in ALS-Quels sont les traitements medicamenteux syptomatiques?" *Revue Neurologique*, Jun. 1, 2006, pp. 4S235-4S243, vol. 162.
Norris, F. H. et al. "Trial of Baclofen in Amyotrophic Lateral Sclerosis" *Archives of Neurology*, Nov. 1, 1979, pp. 715-716, vol. 36.
Lees, A. J. et al. "Baclofen in Parkinson's disease" *Journal of Neurology, Neurosurgery & Psychiatry*, Jan. 1, 1978, pp. 707-708, vol. 41.
Chemidex Pharma Ltd. "Lyflex 5mg/5ml Oral Solution" XP-002476376, retrieved from the internet: http://emc.medicines.org.uk/emc/assets/c/html/DisplayDoc.asp?documentID=14939, Apr. 14, 2008.

(Continued)

*Primary Examiner* — Wu-Cheng Winston Shen
*Assistant Examiner* — Christopher R Stone
(74) *Attorney, Agent, or Firm* — Andrea L. C. Reid; Dechert LLP

(57) ABSTRACT

The present invention relates to compositions and methods for the treatment of the Charcot-Marie-Tooth disease and related disorders.

11 Claims, 17 Drawing Sheets

(56) References Cited

OTHER PUBLICATIONS

Figure 1A:
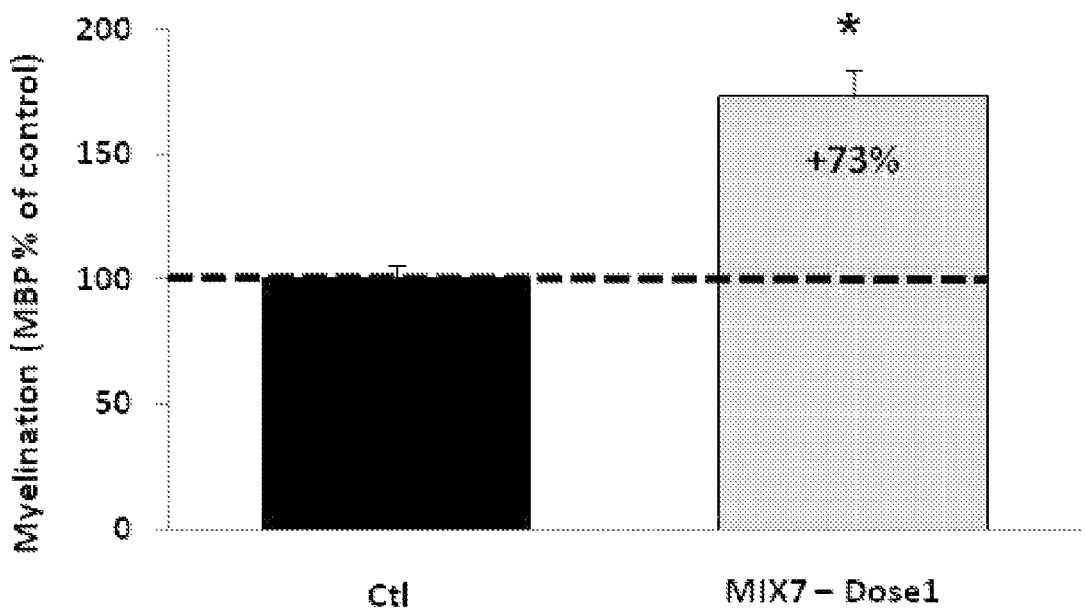
Figure 1B:
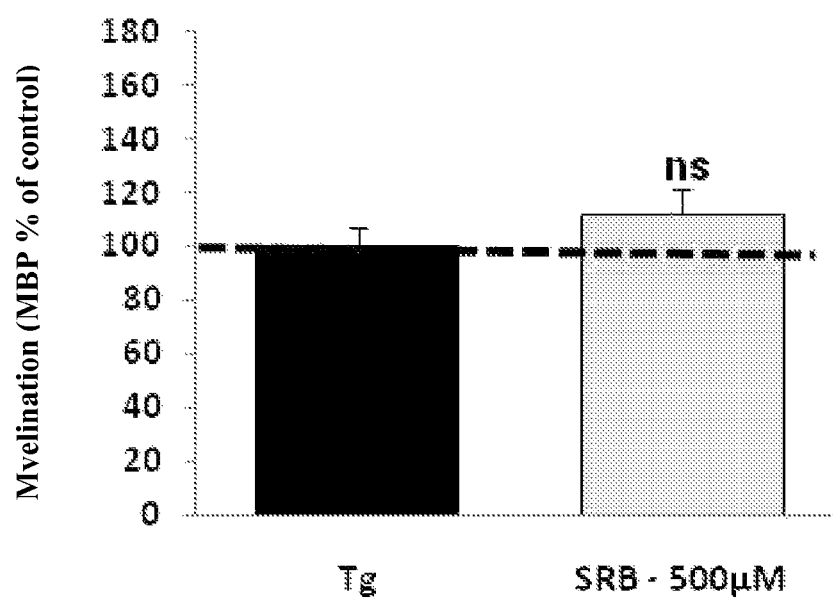
Figure 1C:
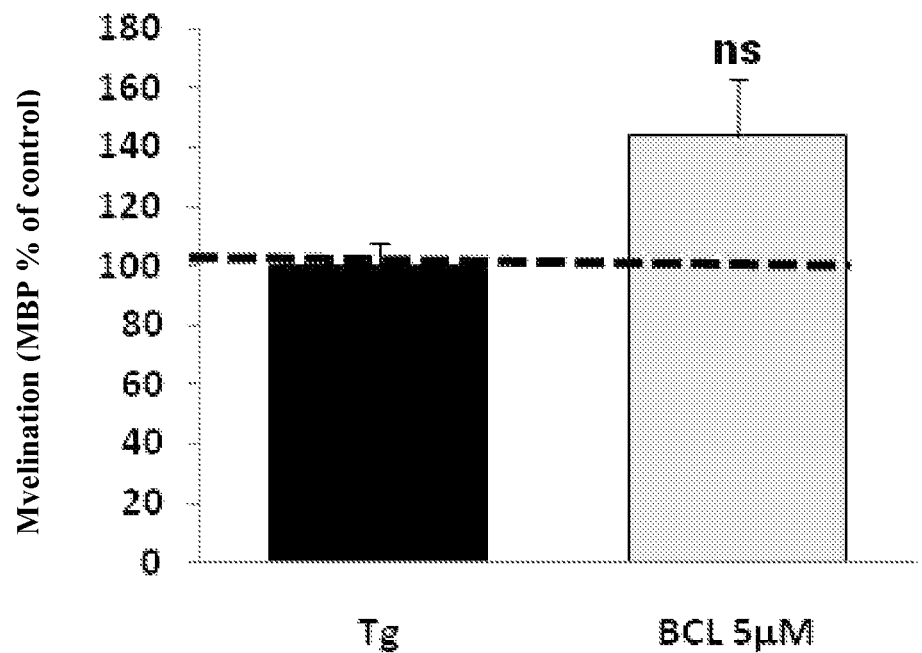
Figure 1D:
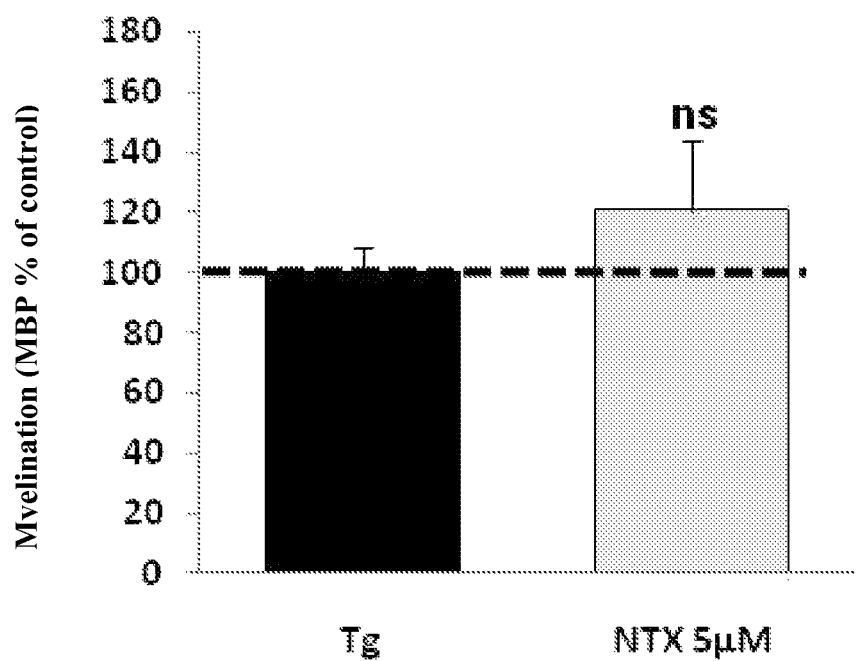

Wilcock, G. K. et al. "A placebo-controlled, double-blind trial of the selective AB-42 lowering agent, flurizan (MPC-7869, (R)-flurbiprofen) in patients with mild to moderate Alzheimer's disease" *Alzheimer's & Dementia: The Journal of the Alzheimer's Association*, Jul. 1, 2005, p. S95, vol. 1, No. 1, Abstract Feb. 1, 2005.

Keltner, J. L. "Myotonic Pupils in Charcot-Marie-Tooth Disease, Successful Relief of Symptoms with 0.025% Pilocarpine" *Achieves of Ophthalmology*, Jan. 1, 1975, pp. 1141-1148, vol. 93, No. 11.

Written Opinion in International Application No. PCT/EP2010/057438, Nov. 4, 2010, pp. 1-11.

Bassi et al., "Encephalomyelitis with Thyrotoxicosis," Journal of Neurology, vol. 218, No Month Listed 1978 (pp. 293-295).

Berenbaum et al., "Synergy, Additivism and Antagonism in Immunosuppression: A Critical Review," Clinical & Experimental Immunology, vol. 28, No Month Listed 1977 (pp. 1-18).

Coffey et al., "Familial Trigeminal Neuralgia and Charcot-Marie-Tooth Neuropathy—Report of Two Families and Review," Surgical Neurology, vol. 35, Jan. 1, 1991 (pp. 49-53).

Colombo et al., "Effects of the Combination of Naltrexone and Baclofen on Acquisition of Alcohol Drinking Behavior in Alcohol-Preferring Rats," Drug and Alcohol Dependence, vol. 77, No. 1, No Month Listed 2005 (pp. 87-91).

Genetics Home Reference: Your Guide to Understanding Genetics Conditions. "Charcot-Marie-Tooth Disease," Dec. 11, 2012 <http://ghr.nlm.nih.gov/condition/charcot-marie-tooth-disease/show/print>(15 pages).

Grandis et al., "Current Therapy for Charcot-Marie-Tooth Disease," Current Treatment Options in Neurology, vol. 7, No. 1, No Month Listed 2005 (pp. 23-31).

International Search Report and Written Opinion issued by the European Patent Office as International Searching Authority for International Application No. PCT/EP2008/066468 mailed Mar. 3, 2009 (14 pages).

International Search Report and Written Opinion issued by the European Patent Office as International Searching Authority for International Application No. PCT/EP2014/061664 mailed Jun. 30, 2014 (10 pages).

Li et al., "Effect of Baclofen Combined with Neural Facilitation Technique on the Reduction of Muscular Spasm in Patients with Spinal Cord Injury," Neural Regeneration Research, vol. 2, No. 8, Aug. 2007 (pp. 510-512).

Magnaghi et al., "GABA Receptor-Mediated Effects in the Peripheral Nervous System—A Cross-Interaction with Neuroactive Steroids," Journal of Molecular Neuroscience, vol. 28, No. 1, No Month Listed 2006 (pp. 89-102).

Mhra, "Baclofen 5MG/5ML Oral Solution," Retrieved from the Internet <http://www.mhra.gov/uk/home/groups/par/documents/websiteresources/con094157.pdf> Aug. 2, 2010 (22 pages).

Pharminfotech, "Baclofen," Formulation in Pharmacy Practice—eMixt, Retrieved from the Internet <http://www.pharminfotech.co.nz/manual/Formulation/mixtures/baclofen.html> Aug. 31, 2011 (2 pages).

RightDiagnosis.com http://www.rightdiagnosis.com/n/neuropathy/subtypes.htm. Accessed Feb. 28, 2014 (pp. 1-9).

Stella et al., "Prodrug Strategies to Overcome Poor Water Solubility," Advanced Drug Delivery Reviews 59, No Month Listed 2007 (pp. 677-694).

Weimer et al., "Medication-Induced Exacerbation of Neuropathy in Charcot-Marie-Tooth Disease," Journal of Neurological Science, vol. 242, No. 1-2, No Month Listed 2006 (pp. 47-54).

\* cited by examiner

| | Groups of performances in inclined plane test | | | p-value (vs TG placebo) |
|---|---|---|---|---|
| | Poor score | Intermediate score | Good score | |
| WT placebo | 11% | 21% | 68% | 0,0003 |
| TG placebo | 60% | 35% | 5% | - |
| Mix7-dose2 | 29% | 41% | 29% | 0,0152 |
| Mix7-dose3 | 11% | 56% | 33% | 0,0020 |

US 9,393,241 B2

COMPOSITIONS FOR TREATING CMT AND RELATED DISORDERS

CROSS-REFERENCE TO RELATED APPLICATIONS

This application is a continuation-in-part of U.S. application Ser. No. 13/375,288 filed Nov. 30, 2011, which is a national stage application of International Patent Application No. PCT/EP2010/057438, filed May 28, 2010, the disclosures of which are hereby incorporated by reference in their entirety, including all figures, tables and amino acid or nucleic acid sequences.

The Sequence Listing for this application is labeled "SeqList.TXT" which was created on Feb. 24, 2014 and is 3 KB. The entire contents of the sequence listing is incorporated herein by reference in its entirety.

The present invention relates to compositions and methods for the treatment of the Charcot-Marie-Tooth disease and related disorders.

Charcot-Marie-Tooth disease ("CMT") is an orphan genetic peripheral poly neuropathy. Affecting approximately 1 in 2,500 individuals, this disease is the most common inherited disorder of the peripheral nervous system. Its onset typically occurs during the first or second decade of life, although it may be detected in infancy. Course of disease is chronic with gradual neuromuscular degeneration. The disease is invalidating with cases of accompanying neurological pain and extreme muscular disability. CMT is one of the best studied genetic pathologies with approximately 30,000 cases in France. While a majority of CMT patients harbour a duplication of a chromosome 17 fragment containing a myelin gene: PMP22 (form CMT1A), two dozens of genes have been implicated in different forms of CMT. Accordingly, although monogenic in origin, this pathology manifests clinical heterogeneity due to possible modulator genes. The genes mutated in CMT patients are clustering around tightly connected molecular pathways affecting differentiation of Schwann cells or neurons or changing interplay of these cells in peripheral nerves.

Mining of publicly available data, describing molecular mechanisms and pathological manifestations of the CMT1A disease, allowed us to prioritize a few functional cellular modules—transcriptional regulation of PMP22 gene, PMP22 protein folding/degradation, Schwann cell proliferation and apoptosis, death of neurons, extra-cellular matrix deposition and remodelling, immune response—as potential legitimate targets for CMT-relevant therapeutic interventions. The combined impact of these deregulated functional modules on onset and progression of pathological manifestations of Charcot-Marie-Tooth justifies a potential efficacy of combinatorial CMT treatment.

International patent application No. PCT/EP2008/066457 describes a method of identifying drug candidates for the treatment of the Charcot-Marie-Tooth disease by building a dynamic model of the pathology and targeting functional cellular pathways which are relevant in the regulation of CMT disease.

International patent application No. PCT/EP2008/066468 describes compositions for the treatment of the Charcot-Marie-Tooth disease which comprise at least two compounds selected from the group of multiple drug candidates.

SUMMARY OF INVENTION

The purpose of the present invention is to provide new therapeutic combinations for treating CMT and related disorders. The invention thus relates to compositions and methods for treating CMT and related disorders, in particular toxic or traumatic neuropathy and amyotrophic lateral sclerosis, using particular drug combinations.

An object of this invention more specifically relates to a composition comprising baclofen, sorbitol and a compound selected from pilocarpine, methimazole, mifepristone, naltrexone, rapamycine, flurbiprofen and ketoprofen, salts or prodrugs thereof, for simultaneous, separate or sequential administration to a mammalian subject.

A particular object of the present invention relates to a composition comprising baclofen, sorbitol and naltrexone, for simultaneous, separate or sequential administration to a mammalian subject.

Another object of the invention relates to a composition comprising (a) rapamycin, (b) mifepristone or naltrexone, and (c) a PMP22 modulator, for simultaneous, separate or sequential administration to a mammalian subject.

In a particular embodiment, the PMP22 modulator is selected from acetazolamide, albuterol, amiloride, aminoglutethimide, amiodarone, aztreonam, baclofen, balsalazide, betaine, bethanechol, bicalutamide, bromocriptine, bumetanide, buspirone, carbachol, carbamazepine, carbimazole, cevimeline, ciprofloxacin, clonidine, curcumin, cyclosporine A, diazepam, diclofenac, dinoprostone, disulfiram, D-sorbitol, dutasteride, estradiol, exemestane, felbamate, fenofibrate, finasteride, flumazenil, flunitrazepam, flurbiprofen, furosemide, gabapentingabapentin, galantamine, haloperidol, ibuprofen, isoproterenol, ketoconazole, ketoprofen, L-carnitine, liothyronine (T3), lithium, losartan, loxapine, meloxicam, metaproterenol, metaraminol, metformin, methacholine, methimazole, methylergonovine, metoprolol, metyrapone, miconazole, mifepristone, nadolol, naloxone, naltrexone; norfloxacin, pentazocine, phenoxybenzamine, phenylbutyrate, pilocarpine, pioglitazone, prazosin, propylthiouracil, raloxifene, rapamycin, rifampin, simvastatin, spironolactone, tacrolimus, tamoxifen, trehalose, trilostane, valproic acid, salts or prodrugs thereof.

Another object of this invention is a composition comprising rapamycin and mifepristone, for simultaneous, separate or sequential administration to a mammalian subject.

A further object of this invention is a composition as disclosed above further comprising one or several pharmaceutically acceptable excipients or carriers (i.e., a pharmaceutical composition).

Another object of the present invention relates to a composition as disclosed above for treating CMT or a related disorder.

A further object of this invention relates to the use of a combination of compounds as disclosed above for the manufacture of a medicament for the treatment of CMT or a related disorder.

A further object of this invention is a method for treating CMT or a related disorder, the method comprising administering to a subject in need thereof an effective amount of a composition as defined above.

A further object of this invention is a method of preparing a pharmaceutical composition, the method comprising mixing the above compounds in an appropriate excipient or carrier.

A more specific object of this invention is a method of treating CMT1A in a subject, the method comprising administering to the subject in need thereof an effective amount of a compound or combination of compounds as disclosed above.

A further specific object of this invention is a method of treating a toxic neuropathy in a subject, the method comprising administering to the subject in need thereof an effective amount of a compound or combination of compounds as disclosed above.

A further specific object of this invention is a method of treating ALS in a subject, the method comprising administering to the subject in need thereof an effective amount of a compound or combination of compounds as disclosed above.

A further specific object of this invention is a method of treating a traumatic neuropathy in a subject, the method comprising administering to the subject in need thereof an effective amount of a compound or combination of compounds as disclosed above.

A further specific object of this invention is a method of promoting nerve regeneration in a subject in need thereof, the method comprising administering to said subject an effective amount of a compound or combination of compounds as disclosed above.

Any of the various uses or methods of treatment disclosed herein can also include an optional step of diagnosing a patient as having CMT or a related disorder, particularly CMT1A, or identifying an individual as at risk of developing CMT or a related disorder, particularly CMT1A.

In this regard, a further object of this invention is a method of treating CMT, particularly CMT1A, the method comprising (1) assessing whether a subject has CMT, particularly CMT1A and (2) treating the subject having CMT, particularly CMT1A with an effective amount of a combination of compounds as described above. Determining whether a subject has CMT, particularly CMT1A, can be done by various tests known per se in the art, such as DNA assays.

The invention may be used for treating CMT or a related disorder in any mammalian subject, particularly human subjects, more preferably CMT1A.

LEGEND TO THE FIGURES

FIGS. 1A-1D. Synergistic effect of drug combination, dose 1: effect of A) Mix7 (dose 1, day 10), B) D-Sorbitol (SRB, 500 µM, day 10), C) (R/S)-Baclofen (BCL, 5 µM, day 10) and D) Naltrexone (NTX, 5 µM, day 10) on MBP expression. *:$p<0.05$: significantly different from control (=ascorbic acid) (One-Way ANOVA followed by Fisher Post-hoc test); ns: not statistically different.

FIGS. 2A-2D. Synergistic effect of drug combination, dose 6 A) Mix7 (dose 6, day 10), B) SRB (160 nM, day 10), C) BCL (1.6 nM, day 10) and D) NTX (1.6 nM, day 10) on MBP expression. *:$p<0.05$: significantly different from control (=ascorbic acid) (One-Way ANOVA followed by Fisher Post-hoc test); ns: not statistically different.

Figure 3A:
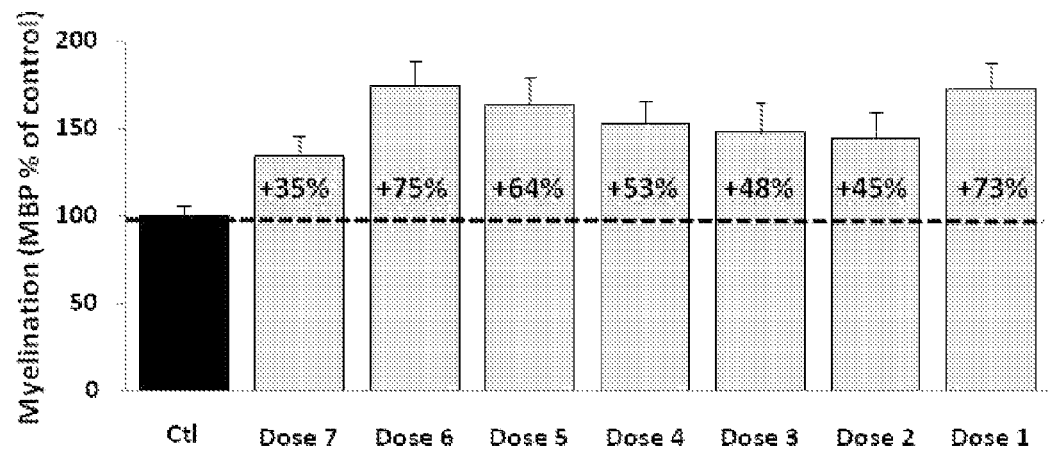
Figure 3B:
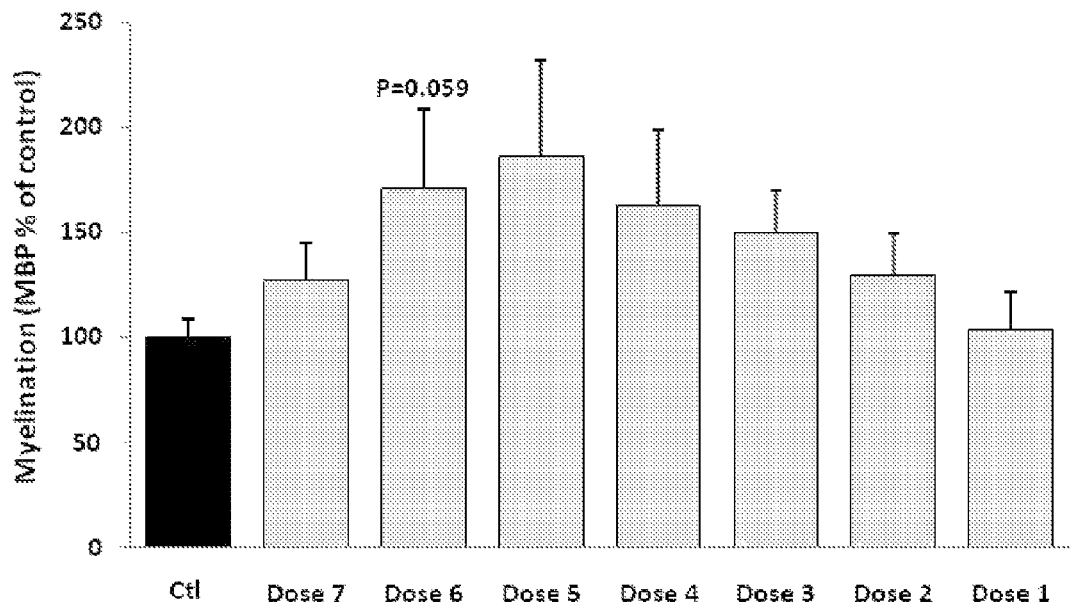

FIGS. 3A-3B. Positive effect of Mix7 (7 doses) A) on day 10 and B) on day 11 in co-incubation with ascorbic acid in PMP22 TG co-cultures on MBP expression in percentage of control (=ascorbic acid). One-Way ANOVA followed by Fisher post-hoc test.

Figure 4:
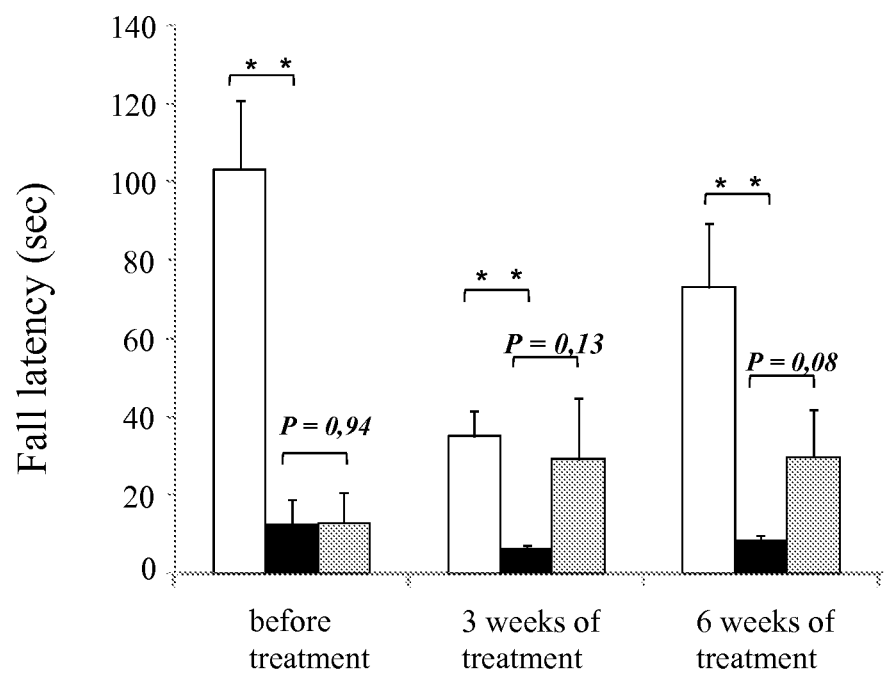

FIG. 4. Positive effect on male rats of the 3 and 6 week treatment with Mix1 measured using bar test. Latencies were measured as the mean of two first assays of the tests (white bars represent control rats treated with placebo; black bars represent transgenic rats treated with placebo; grey bars represent transgenic rats treated with Mix1. **$p<0.01$. Statistics are realised with the Student bilateral test).

Figure 5:
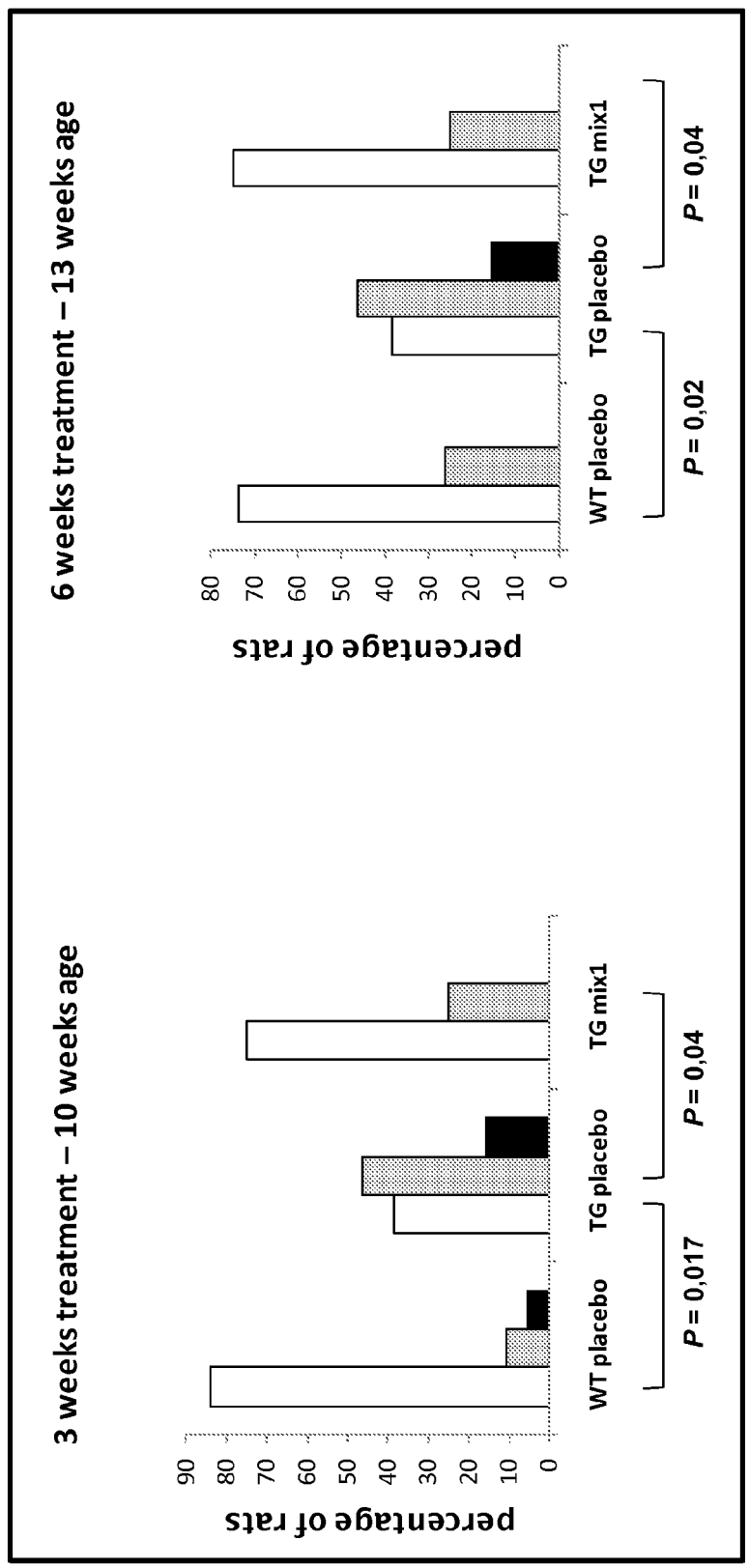

FIG. 5. Positive effect on gait of male rats of the 3 and 6-week (respectively left and right graph) treatment with Mix1 composition (white bars represent fluid gait; grey bars represent not fluid gait); black bars represent rats with a severe incapacity to walk. Statistics are realised with the Student bilateral test).

Figure 6:
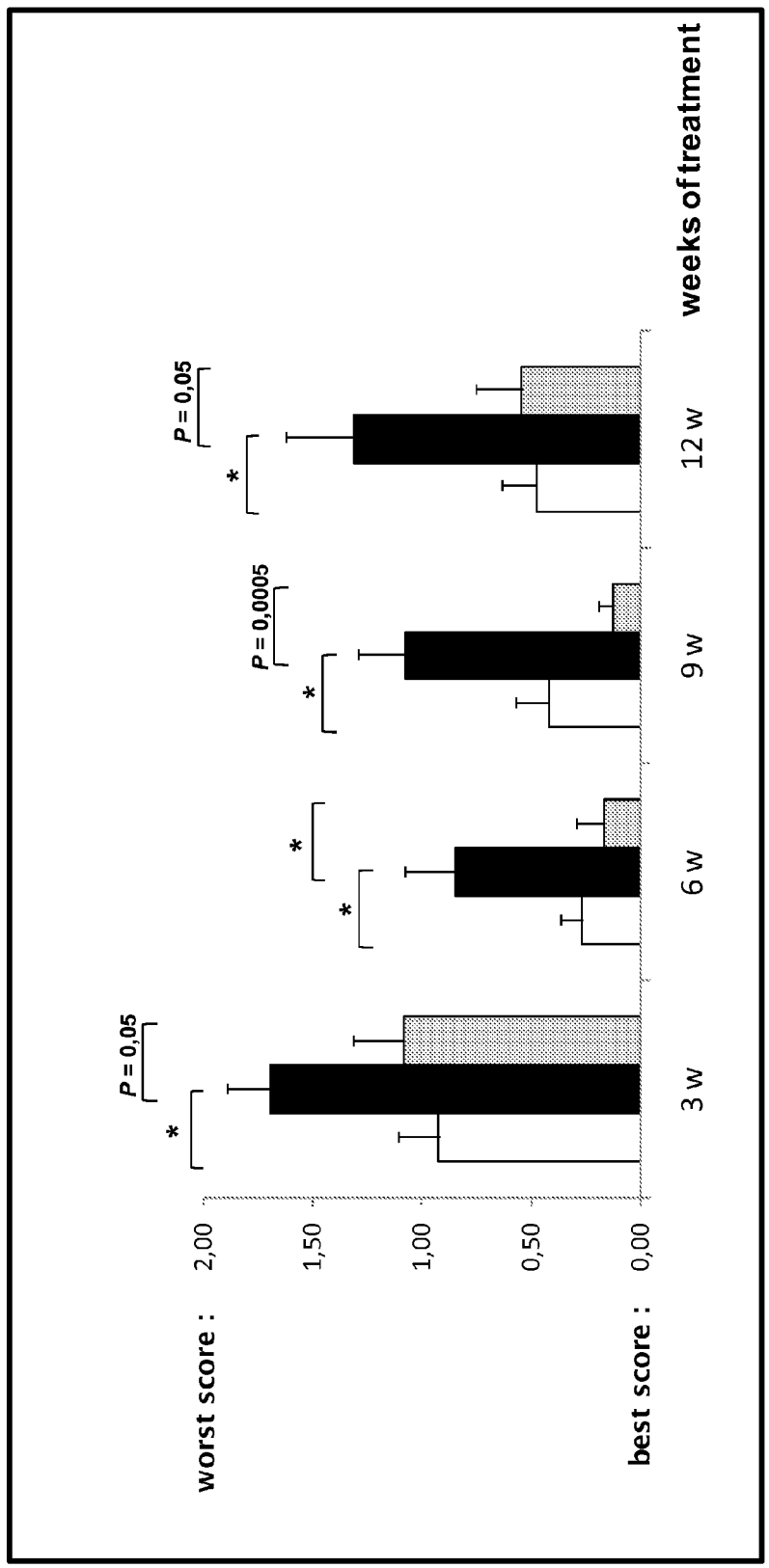

FIG. 6. Positive effect on male rats of the Mix1 composition in rats using inclined plane test (25°). Rats were examined after 3, 6, 9 and 12 weeks of treatment (white bars represent control rats treated with placebo; black bars represent transgenic rats treated with placebo; grey bars represent transgenic rats treated with Mix1. *$p<0.05$. Statistics are realised with the Student bilateral test).

Figure 7:
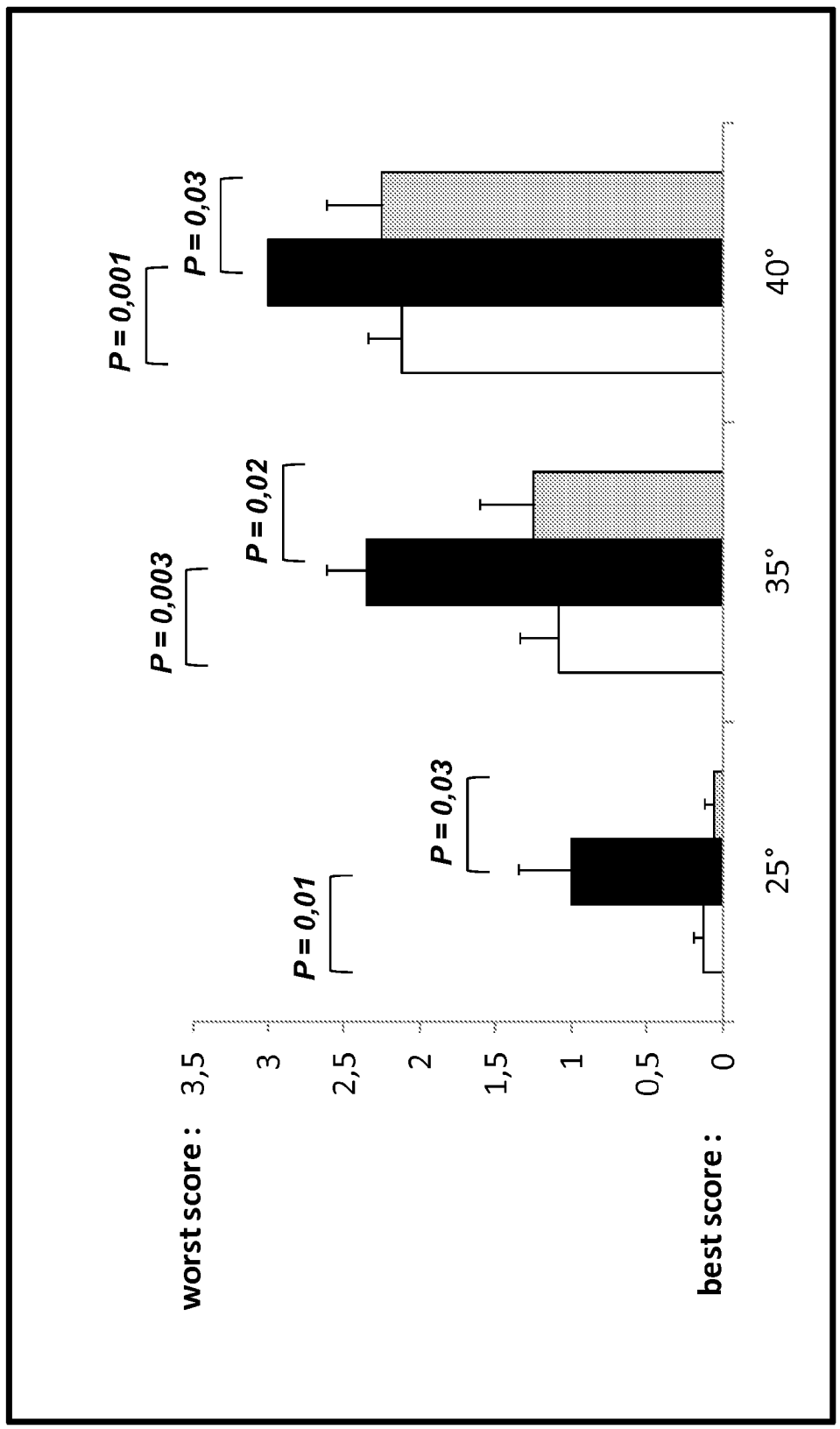

FIG. 7. Positive effect on female rats of the 3 week treatment with the Mix2 composition in rats, using an inclined plane test (white bars represent control rats treated with placebo; black bars represent transgenic rats treated with placebo; grey bars represent transgenic rats treated with Mix2. **$p<0.01$. Statistics are realised with the Student bilateral test).

Figure 8:
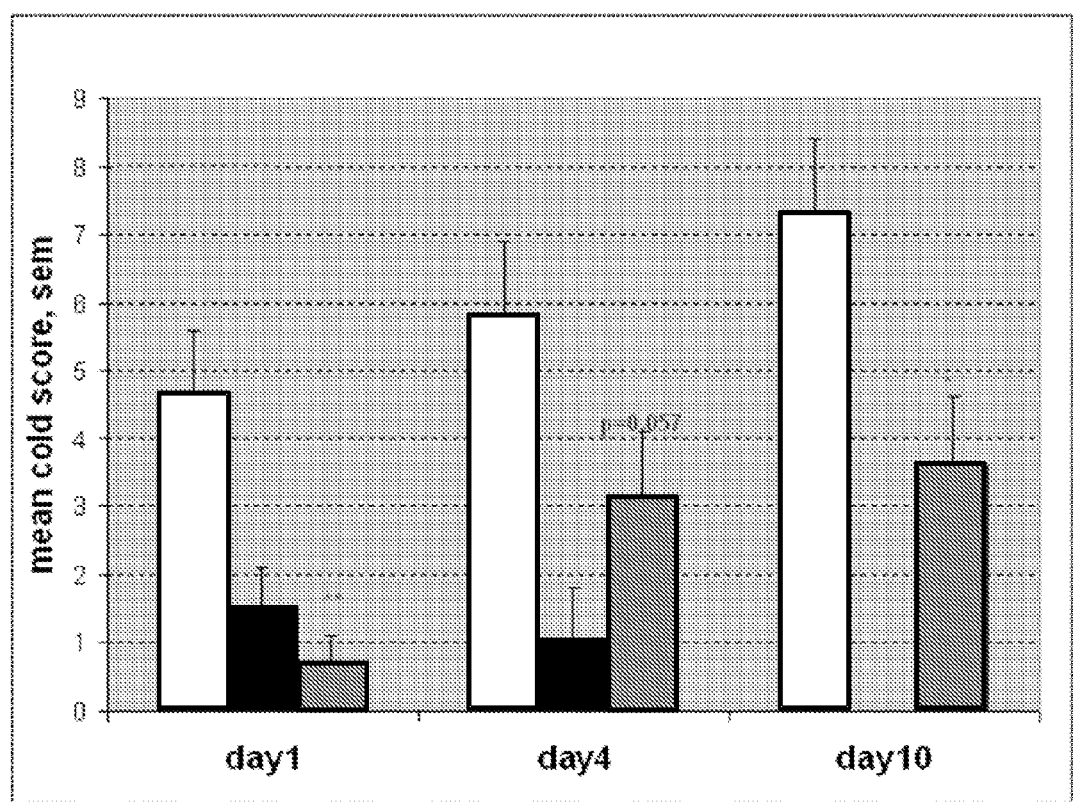

FIG. 8. Protective effect on male rats of Mix1 on oxaliplatin-induced neuropathy (white bars represent wild type rats treated with placebo; black bars represent wild type rats treated with reference product gabapentin; grey bars represent wild type rats treated with Mix1. *$p<0.05$; **$p<0.01$. Statistics are realised with the Student bilateral test).

Figure 9:
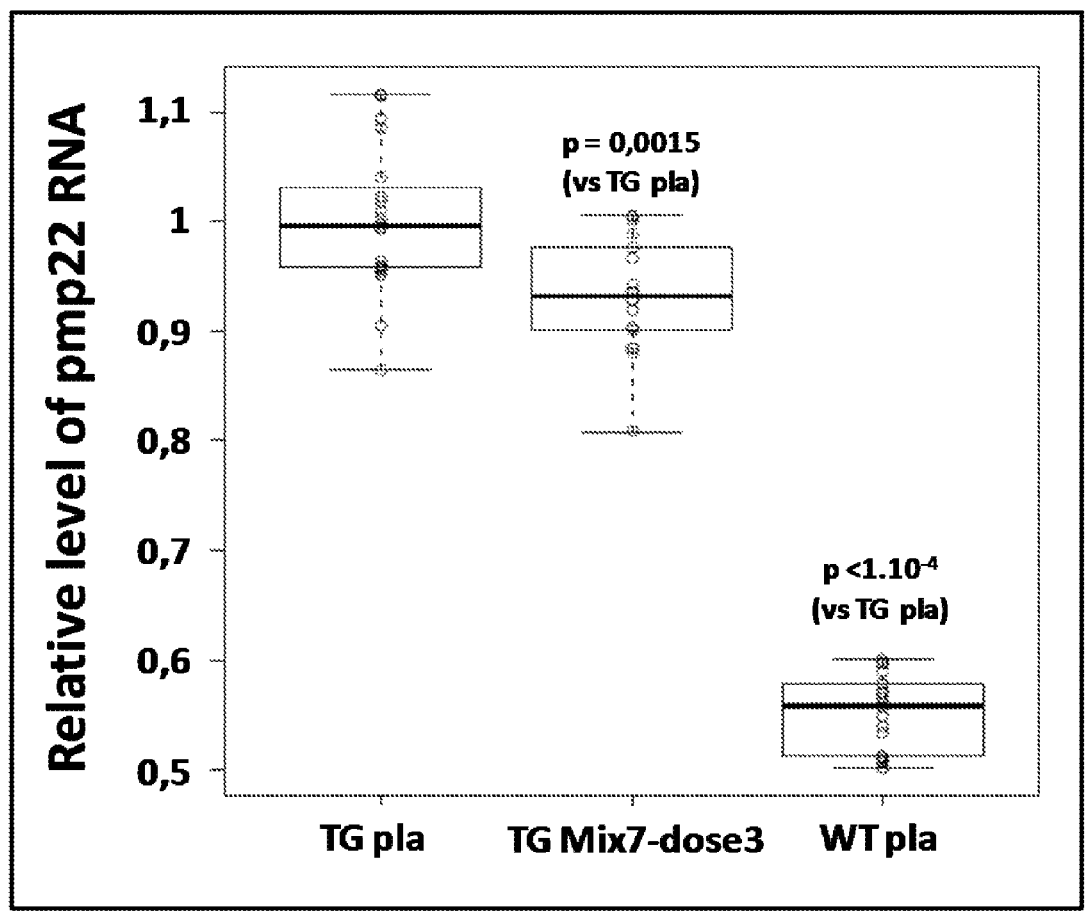

FIG. 9. Significant decrease of pmp22 RNA expression in treated transgenic animals compared to PMP22 transgenic rats, observed after 9 weeks of treatment with the Mix7-dose 3 (MPZ as reference gene, Sereda et al., 1996) ($p=0.0015$). The transgene integration and the overexpression of pmp22 gene have also been confirmed; pmp22 RNA in transgenic PMP22 rats was 1.8 fold overexpressed compared to their wild type littermates controls ($p<1\ 10^{-4}$). Extraction of pmp22 RNA was performed on sciatic nerves of 16 weeks old male rats (n=18 for the Wild Type, n=20 for the transgenic rats and n=18 for TG treated with Mix7-dose3). Statistical analysis was performed by using the Welch t-test.

Figures 10, 11:
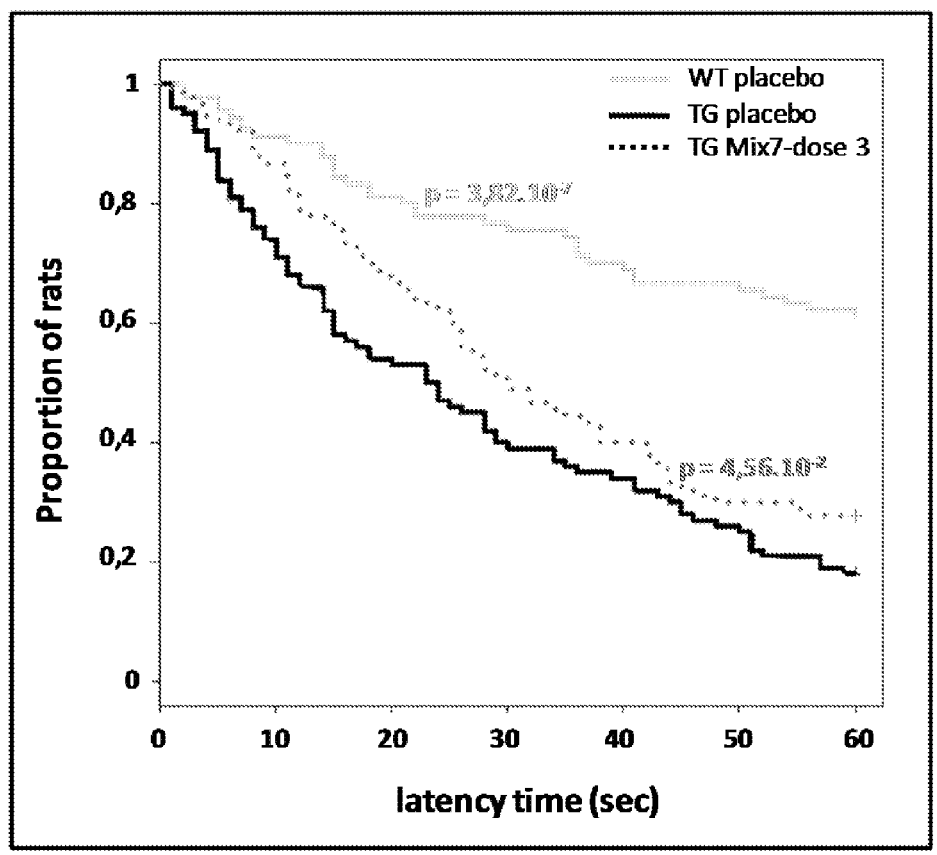

FIG. 10. A clustering analysis was performed on the inclined plane test score at 35° (to distribute in the poor, intermediate and good performance classes at all time points of evaluation (3, 6 and 9 weeks of treatment analyzed together). A significant difference was observed between WT and TG placebo: 68% of WT belonged to the good performances group and only 5% of TG placebo belonged to this group ($p=0.0003$). Mix7-dose 2 and dose 3 improved the performances of TG rats. Statistical analysis were performed by applying a trend-test at the 5% significance level (n=18 for WT placebo rats, n=20 for TG placebo rats, n=17 for TG treated with Mix7-dose 2, n=18 for TG treated with Mix7-dose3).

FIG. 11. The fall latencies of TG rats in the bar test after 9 weeks of treatment with Mix7-dose3 were analyzed using a Cox model with a sandwich variance estimator, and compared to the reference TG placebo by applying a log rank-test at the 5% significance level. Mix7-dose 3 significantly increased the fall latency of TG rats after 9 weeks of treatment.

Figure 12:
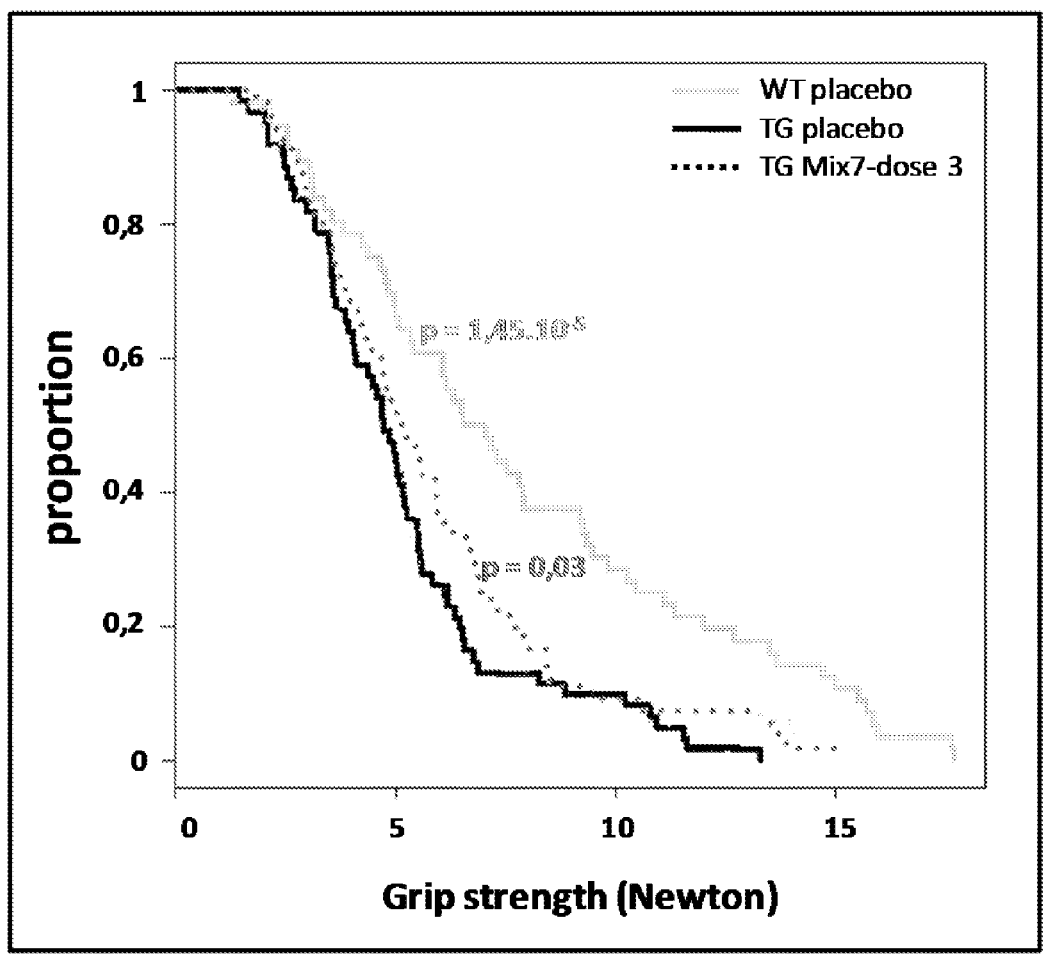

FIG. 12. The grip strength of groups of wild type, transgenic placebo and transgenic animals treated with Mix7-dose 3 daily for 9 weeks was modelized using a Cox model with a sandwich variance estimator over all the times after treatment (3, 6 and 9 weeks) and compared to the reference TG placebo by applying a log rank-test at the 5% significance level. The corresponding p-values were presented on Kaplan-Meier curves A significant decrease of the fore paws grip strength of transgenic placebo rats was observed (black plain line, n=21) compared to WT rats (grey plain line, $p=1.45\ 10^{-5}$, n=19). The treatment with Mix7-dose 3 significantly increased the strength of the fore paws (black dashed line; $p=0.03$, n=18).

Figure 13:
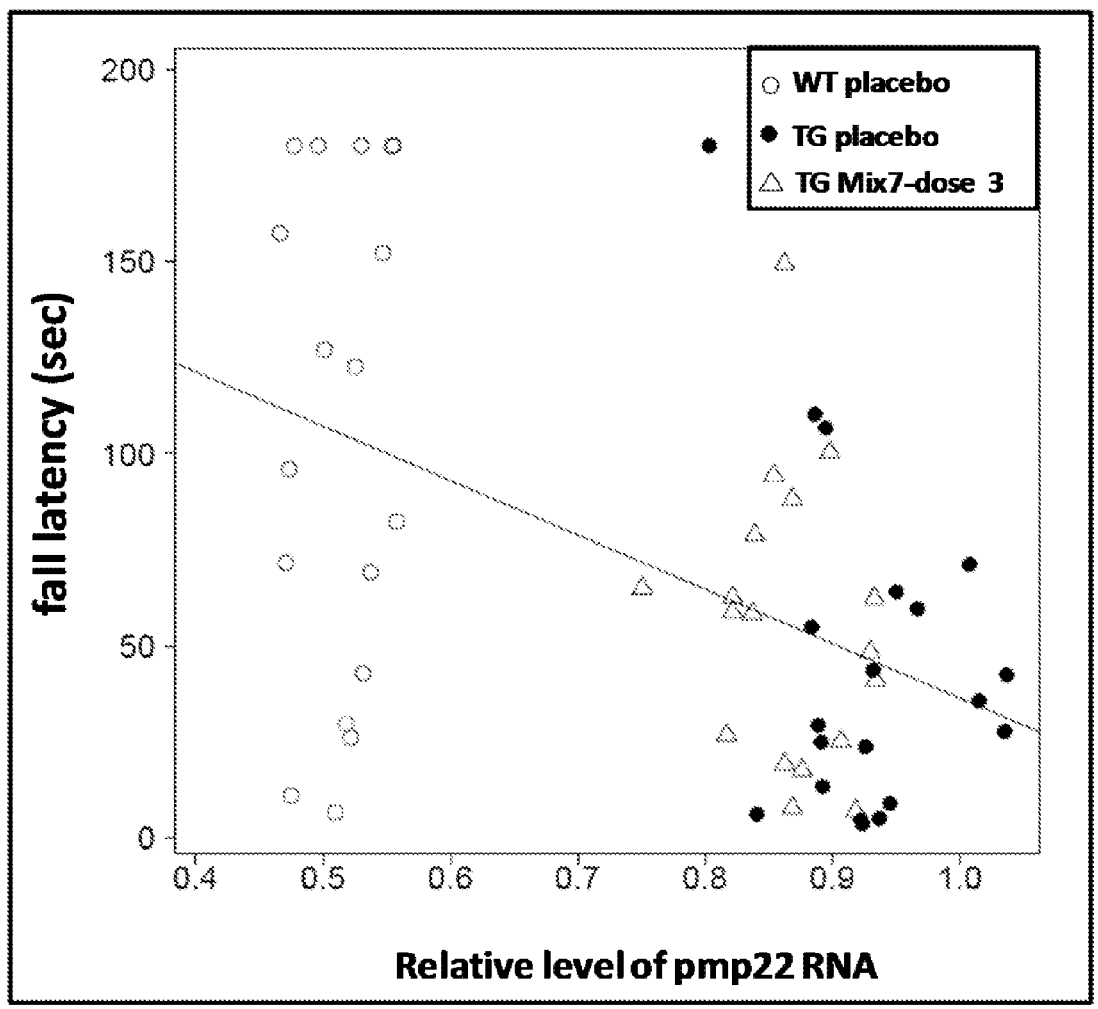

FIG. 13. A Pearson correlation test showed a significant correlation between the fall latency time in the bar test (after 9 weeks of treatment) and the pmp22 RNA expression level:

p=1.6 10$^{-4}$ (WT, TG placebo and TG treated with the Mix7-dose 3 analysed together); p=0.07 (TG placebo and TG treated with the Mix7-dose 3 analysed together). The lower the pmp22 RNA expression was, the better the bar test performances were. Male rats were 16 weeks old (n=18 for WT rats, white circles; n=20 for the TG placebo, black circles and n=18 for TG treated with the Mix7-dose3, white triangles).

Figure 14:
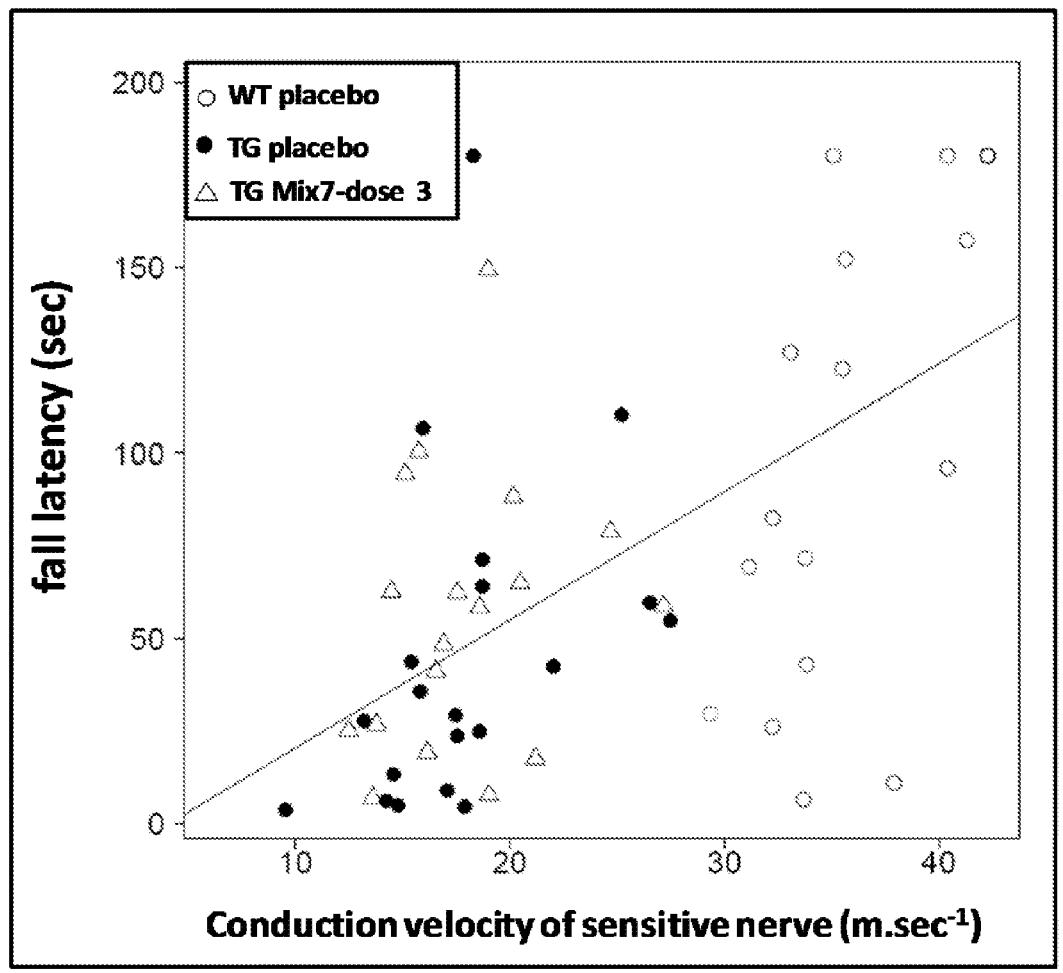

FIG. 14. A Pearson correlation test showed a significant correlation between the fall latency time in the bar test (after 9 weeks of treatment) and the conduction velocity of the sensitive nerve (NCV): p=1.34 10-6 (WT, TG placebo and TG treated with Mix7-dose3 analysed together) and p=0.04 (TG placebo and TG treated with Mix7-dose3 analysed together). The higher the conduction velocity was, the better the performances in bar test were. Male rats were 16 weeks old (n=18 for WT rats, white circles; n=20 for the TG placebo, black circles and n=18 for TG treated with the Mix7-dose3, white triangles).

FIGS. 15A-15C. Mix7 (dose3) treatment of nerve-crushed mice restores nerve physiology and improves axonal and myelin integrity. A) A 3-week oral treatment with mix7 increased the amplitude of CMAP (sciatic nerve/gastrocnemius) of sciatic nerve crushed male mice. (n=10 for each sham, crush/vehicle and crush/mix7 group). B) A 6-week oral treatment with mix7 significantly improved axon calibre size. C) The distribution of G-ratio (ratio of the inner axonal diameter to the total outer—axonal and myelin—diameter) according to the axon diameter in crushed mice showed hypermyelination of smaller and hypomyelination of larger axons. A 6-week oral treatment with mix7 significantly improved the distribution of G-ratio of crushed mice (B) and C), n=6 for each group) (t-test. *p<0.05, p<0.01, *p<0.001. All data are shown as mean+s.e.m.).

Figure 16:
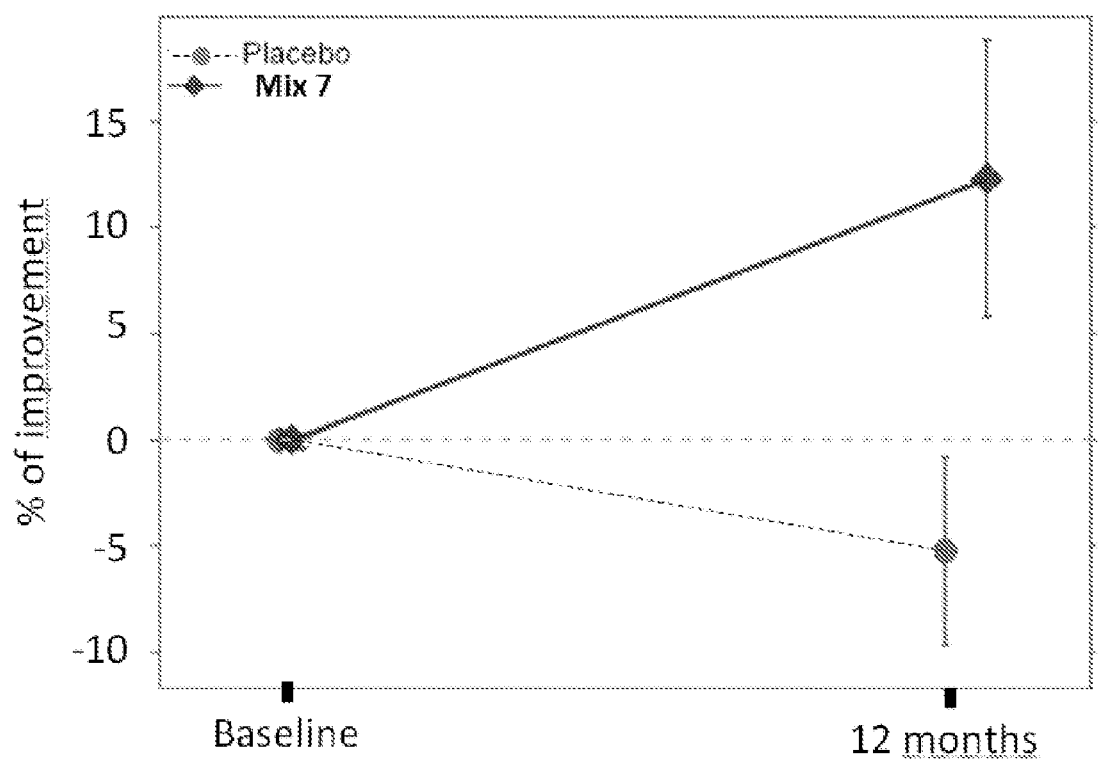

FIG. 16. Mix7 improved significantly (P<0.05) neuropathy disabilities in CMT1A patients in a 12 months trial (mean±s.e.m). In the Mix7 treated group (solid line), ONLS improved by more than 10% when compared to the baseline score, whereas in the placebo group (dashed line), ONLS decreased by about 5% when compared to the baseline score.

DETAILED DESCRIPTION OF THE INVENTION

The present invention provides new therapeutic approaches for treating CMT or CMT-related disorders. The invention discloses novel drug combinations which allow an effective correction of such diseases and may be used in any mammalian subject.

Within the context of this invention, CMT includes CMT1A, CMT1B, CMT1C, CMT1D, CMT1X, CMT2A, CMT2B, CMT2D, CMT2E, CMT2-P0, CMT4A, CMT4B1, CMT4B2, CMT4D, CMT4F, CMT4, or AR-CMT2A, more preferably CMT1a.

Within the context of the present invention, the term "CMT related disorder" designates other diseases associated with abnormal expression of PMP22 leading to abnormal myelination and loss of neurons. The term "CMT related disorder" more particularly includes Alzheimer's disease (AD), senile dementia of AD type (SDAT), Parkinson's disease, Lewy body dementia, vascular dementia, autism, mild cognitive impairment (MCI), age-associated memory impairment (AAMI) and problem associated with ageing, post-encephalitic Parkinsonism, schizophrenia, depression, bipolar disease and other mood disorders, Huntington's disease, motor neuron diseases including amyotrophic lateral sclerosis (ALS), multiple sclerosis, neuropathies, including idiopathic neuropathies, diabetic neuropathy, toxic neuropathies, including neuropathy induced by drug treatments, neuropathies provoked by HIV, radiation, heavy metals or vitamin deficiency states, or traumatic neuropathies (e.g., resulting from a mechanical neuronal insult), prion-based neurodegeneration, including Creutzfeld-Jakob disease (CJD), bovine spongiform encephalopathy (BSE), GSS, FFI, Kuru and Alper's syndrome.

In a preferred embodiment, "CMT related disorder" designates a toxic or traumatic neuropathy, particularly drug-induced neuropathies, ALS or neuropathies resulting from a mechanical neuronal insult.

Within the context of the invention, "mechanical neuronal insults" refers to a direct physical damage to the nerve either in the central nervous system (CNS) or in the peripheral nervous system (PNS). Damages to the PNS can be ranked according to the stage of the neuronal insult. The present invention is suited for treating nerve injuries ranking from neurapraxia (condition where only signalling ability of the nerve is impaired), axonometsis (injury implying damages to the axons, without impairing surrounding connective tissues of the nerves), and also neurotmesis (injury damaging both axon and surrounding tissues).

Damages to the CNS encompass spinal cord injuries as well as traumatic brain injuries. Traumatic brain injuries can be either primary (i.e., resulting directly from the trauma) or secondary injuries (i.e., which are the consequences of the trauma). Spinal cord injuries can be ranked according the extent of sensory and motor disabilities, as set up in the *International Standards for Neurological Classification of Spinal Cord Injury* (Kirshblum et al., 2011).

As used herein, "treatment" of a disorder includes the therapy, prevention, prophylaxis retardation or reduction of pain provoked by the disorder. The term treatment includes in particular the control of disease progression and associated symptoms. In particular, the treatment of a CMT or related neuropathy according to the invention includes a prevention or retardation or reduction or improvement in a motor, autonomic and/or sensory impairment caused by such diseases. Motor symptoms include uncontrollable contraction, fasciculation weakness, or complete unresponsiveness of muscle(s) innervated by injured nerves. Autonomic symptoms may affect cardiovascular system, sudomotor, thermoregulatory, urinary, gastrointestinal, and/or reproductive systems. Sensory symptoms include pain, numbness, or a loss of sensation in the areas innervated by the injured nerves.

"Nerve regeneration" encompasses promotion of myelination, of axonal growth and/or restoration of either morphological or functional features of the nerve.

Also, the term "compound" designates the chemical compounds as specifically named in the application, as well as any pharmaceutically composition with acceptable salt, hydrate, ester, ether, isomers, racemate, conjugates, pro-drugs thereof. The compounds listed in this application may also be identified with its corresponding CAS number.

Thus, the preferred compounds used in the invention are baclofen (CAS 1134-47-0) and its possible salts, enantiomers, racemates, prodrugs and derivatives; sorbitol (CAS 50-70-4) and its possible salts, enantiomers, racemates, prodrugs and derivatives; naltrexone (CAS 16590-41-3) and its possible salts, enantiomers, racemates, prodrugs and derivatives; mifepristone (CAS 84371-65-3) and its possible salts, enantiomers, racemates, prodrugs and derivatives; pilocarpine (CAS 54-71-7) and its possible salts, enantiomers, racemates, prodrugs and derivatives; methimazole (CAS 60-56-0) and its possible salts, enantiomers, racemates, prodrugs and derivatives; ketoprofen (CAS 22071-15-4) and its possible salts, enantiomers, racemates, prodrugs and derivatives; flurbiprofen (5104-49-4) and its possible salts, enantiomers, racemates, prodrugs and derivatives and rapamycin (CAS 53123-88-9) and its possible salts, enantiomers, racemates, prodrugs and derivatives.

Further compounds used in the invention are acetazolamide (CAS 59-66-5) and its possible salts, enantiomers, prodrugs and derivatives; albuterol (CAS 18559-94-9) and its possible salts, enantiomers, prodrugs and derivatives; amiloride (CAS 2016-88-8) and its possible salts, enantiomers, prodrugs and derivatives; aminoglutethimide (CAS 125-84-8) and its possible salts, enantiomers, prodrugs and derivatives; amiodarone (CAS 1951-25-3) and its possible salts, enantiomers, prodrugs and derivatives; aztreonam (CAS 78110-38-0) and its possible salts, enantiomers, prodrugs and derivatives; baclofen (CAS 1134-47-0) and its possible salts, enantiomers, prodrugs and derivatives; balsalazide (CAS 80573-04-2) and its possible salts, enantiomers, prodrugs and derivatives; betaine (CAS 107-43-7) and its possible salts, enantiomers, prodrugs and derivatives; bethanechol (CAS 674-38-4) and its possible salts, enantiomers, prodrugs and derivatives; bicalutamide (CAS 90357-06-5) and its possible salts, enantiomers, prodrugs and derivatives; bromocriptine (CAS 25614-03-3) and its possible salts, enantiomers, prodrugs and derivatives; bumetanide (CAS 28395-03-1) and its possible salts, enantiomers, prodrugs and derivatives; buspirone (CAS 36505-84-7) and its possible salts, enantiomers, prodrugs and derivatives; carbachol (CAS 51-83-2) and its possible salts, enantiomers, prodrugs and derivatives; carbamazepine (CAS 298-46-4) and its possible salts, enantiomers, prodrugs and derivatives; carbimazole (CAS 22232-54-8) and its possible salts, enantiomers, prodrugs and derivatives; cevimeline (CAS 107233-08-9) and its possible salts, enantiomers, prodrugs and derivatives; ciprofloxacin (CAS 85721-33-1) and its possible salts, enantiomers, prodrugs and derivatives; clonidine (CAS 4205-90-7) and its possible salts, enantiomers, prodrugs and derivatives; curcumin (CAS 458-37-7) and its possible salts, enantiomers, prodrugs and derivatives; cyclosporine A (CAS 59865-13-3) and its possible salts, enantiomers, prodrugs and derivatives; diazepam (CAS 439-14-5) and its possible salts, enantiomers, prodrugs and derivatives; diclofenac (CAS 15307-86-5) and its possible salts, enantiomers, prodrugs and derivatives; dinoprostone (CAS 363-24-6) and its possible salts, enantiomers, prodrugs and derivatives; disulfiram (CAS 97-77-8) and its possible salts, enantiomers, prodrugs and derivatives; D-sorbitol (CAS 50-70-4) and its possible salts, enantiomers, prodrugs and derivatives; dutasteride (CAS 164656-23-9) and its possible salts, enantiomers, prodrugs and derivatives; estradiol (CAS 50-28-2) and its possible salts, enantiomers, prodrugs and derivatives; exemestane (CAS 107868-30-4) and its possible salts, enantiomers, prodrugs and derivatives; felbamate (CAS 25451-15-4) and its possible salts, enantiomers, prodrugs and derivatives; fenofibrate (CAS 49562-28-9) and its possible salts, enantiomers, prodrugs and derivatives; finasteride (CAS 98319-26-7) and its possible salts, enantiomers, prodrugs and derivatives; flumazenil (CAS 78755-81-4) and its possible salts, enantiomers, prodrugs and derivatives; flunitrazepam (CAS 1622-62-4) and its possible salts, enantiomers, prodrugs and derivatives; flurbiprofen (CAS 5104-49-4) and its possible salts, enantiomers, prodrugs and derivatives; furosemide (CAS 54-31-9) and its possible salts, enantiomers, prodrugs and derivatives; gabapentin (CAS 60142-96-3) and its possible salts, enantiomers, prodrugs and derivatives; galantamine (CAS 357-70-0) and its possible salts, enantiomers, prodrugs and derivatives; haloperidol (CAS 52-86-8) and its possible salts, enantiomers, prodrugs and derivatives; ibuprofen (CAS 15687-27-1) and its possible salts, enantiomers, prodrugs and derivatives; isoproterenol (CAS 7683-59-2) and its possible salts, enantiomers, prodrugs and derivatives; ketoconazole (CAS 65277-42-1) and its possible salts, enantiomers, prodrugs and derivatives; ketoprofen (CAS 22071-15-4) and its possible salts, enantiomers, prodrugs and derivatives; L-carnitine (CAS 541-15-1) and its possible salts, enantiomers, prodrugs and derivatives; liothyronine (T3) (CAS 6893-02-3) and its possible salts, enantiomers, prodrugs and derivatives; lithium (CAS 7439-93-2) and its possible salts, enantiomers, prodrugs and derivatives; losartan (CAS 114798-26-4) and its possible salts, enantiomers, prodrugs and derivatives; loxapine (CAS 1977-10-2) and its possible salts, enantiomers, prodrugs and derivatives; meloxicam (CAS 71125-38-7) and its possible salts, enantiomers, prodrugs and derivatives; metaproterenol (CAS 586-06-1) and its possible salts, enantiomers, prodrugs and derivatives; metaraminol (CAS 54-49-9) and its possible salts, enantiomers, prodrugs and derivatives; metformin (CAS 657-24-9) and its possible salts, enantiomers, prodrugs and derivatives; methacholine (CAS 55-92-5) and its possible salts, enantiomers, prodrugs and derivatives; methimazole (CAS 60-56-0) and its possible salts, enantiomers, prodrugs and derivatives; methylergonovine (CAS 113-42-8) and its possible salts, enantiomers, prodrugs and derivatives; metoprolol (CAS 37350-58-6) and its possible salts, enantiomers, prodrugs and derivatives; metyrapone (CAS 54-36-4) and its possible salts, enantiomers, prodrugs and derivatives; miconazole (CAS 22916-47-8) and its possible salts, enantiomers, prodrugs and derivatives; mifepristone (CAS 84371-65-3) and its possible salts, enantiomers, prodrugs and derivatives; nadolol (CAS 42200-33-9) and its possible salts, enantiomers, prodrugs and derivatives; naloxone (CAS 465-65-6) and its possible salts, enantiomers, prodrugs and derivatives; naltrexone (CAS 16590-41-3) and its possible salts, enantiomers, prodrugs and derivatives; norfloxacin (CAS 70458-96-7) and its possible salts, enantiomers, prodrugs and derivatives; pentazocine (CAS 359-83-1) and its possible salts, enantiomers, prodrugs and derivatives; phenoxybenzamine (CAS 59-96-1) and its possible salts, enantiomers, prodrugs and derivatives; phenylbutyrate (CAS 1821-12-1) and its possible salts, enantiomers, prodrugs and derivatives; pilocarpine (CAS 54-71-7) and its possible salts, enantiomers, prodrugs and derivatives; pioglitazone (CAS 111025-46-8) and its possible salts, enantiomers, prodrugs and derivatives; prazosin (CAS 19216-56-9) and its possible salts, enantiomers, prodrugs and derivatives; propylthiouracil (CAS 51-52-5) and its possible salts, enantiomers, prodrugs and derivatives; raloxifene (CAS 84449-90-1) and its possible salts, enantiomers, prodrugs and derivatives; rapamycin (CAS 53123-88-9) and its possible salts, enantiomers, prodrugs and derivatives; rifampin (CAS 13292-46-1) and its possible salts, enantiomers, prodrugs and derivatives; simvastatin (CAS 79902-63-9) and its possible salts, enantiomers, prodrugs and derivatives; spironolactone (CAS 52-01-7) and its possible salts, enantiomers, prodrugs and derivatives; tacrolimus (CAS 104987-11-3) and its possible salts, enantiomers, prodrugs and derivatives; tamoxifen (CAS 10540-29-1) and its possible salts, enantiomers, prodrugs and derivatives; trehalose (CAS 99-20-7) and its possible salts, enantiomers, prodrugs and derivatives; trilostane (CAS 13647-35-3) and its possible salts, enantiomers, prodrugs and derivatives; valproic acid (CAS 99-66-1) and its possible salts, enantiomers, prodrugs and derivatives.

The term "combination" designates a treatment wherein several drugs are co-administered to a subject to cause a biological effect. In a combined therapy, the drugs may be administered together or separately, at the same time or sequentially. Also, the drugs may be administered through different routes and protocols.

The invention now discloses the identification and activities of particular drug combinations which provide an efficient treatment for CMT. More specifically, the invention discloses novel ternary combinations which provide a significant effect in vitro and in vivo on CMT or CMT related disorders.

In this regard, the invention relates to a composition comprising baclofen, sorbitol and a compound selected from pilocarpine, methimazole, mifepristone, naltrexone, rapamycine, flurbiprofen and ketoprofen, salts, enantiomers, racemates, or prodrugs thereof.

More preferably, the invention relates to a composition comprising baclofen, sorbitol and a compound selected from pilocarpine, methimazole, mifepristone, naltrexone, and ketoprofen.

In the most preferred embodiment, the present invention relates to a composition comprising naltrexone, baclofen and sorbitol, for simultaneous, separate or sequential administration to a mammalian subject.

Preferably, in the above compositions, sorbitol is D-sorbitol and baclofen is RS-baclofen or S-baclofen, more preferably RS-baclofen.

Another preferred object of the invention relates to a composition comprising:
(a) rapamycin,
(b) mifepristone or naltrexone, and
(c) a PMP22 modulator,
for simultaneous, separate or sequential administration to a mammalian subject.

Another preferred object of this invention is a composition comprising:
(a) rapamycin,
(b) mifepristone, and
(c) a PMP22 modulator,
for simultaneous, separate or sequential administration to a mammalian subject.

The PMP22 modulator may be any compound that modulates PMP22 pathway in a cell and essentially causes or contributes to normalization of myelin organization and/or inhibition of neuron loss. The PMP22 modulator may be selected from acetazolamide, albuterol, amiloride, aminoglutethimide, amiodarone, aztreonam, baclofen, balsalazide, betaine, bethanechol, bicalutamide, bromocriptine, bumetanide, buspirone, carbachol, carbamazepine, carbimazole, cevimeline, ciprofloxacin, clonidine, curcumin, cyclosporine A, diazepam, diclofenac, dinoprostone, disulfiram, D-sorbitol, dutasteride, estradiol, exemestane, felbamate, fenofibrate, finasteride, flumazenil, flunitrazepam, flurbiprofen, furosemide, gabapentin, galantamine, haloperidol, ibuprofen, isoproterenol, ketoconazole, ketoprofen, L-carnitine, liothyronine (T3), lithium, losartan, loxapine, meloxicam, metaproterenol, metaraminol, metformin, methacholine, methimazole, methylergonovine, metoprolol, metyrapone, miconazole, mifepristone, nadolol, naloxone, naltrexone, norfloxacin, pentazocine, phenoxybenzamine, phenylbutyrate, pilocarpine, pioglitazone, prazosin, propylthiouracil, raloxifene, rapamycin, rifampin, rimvastatin, spironolactone, tacrolimus, tamoxifen, trehalose, trilostane, valproic acid salts or prodrugs thereof.

In a preferred embodiment, compound (c) is selected from pilocarpine, methimazole and baclofen. In this regard, a most preferred composition of this invention comprises:
(a) rapamycin,
(b) mifepristone, and
(c) a compound selected from pilocarpine, methimazole and baclofen,
for simultaneous, separate or sequential administration to a mammalian subject.

Specific examples of such compositions include compositions comprising:
rapamycin, mifepristone and pilocarpine,
rapamycin, mifepristone and baclofen,
rapamycin, mifepristone and methimazole or
rapamycin, naltrexone and methimazole.

The experimental section shows these particular drug combinations are able to efficiently correct PMP22 expression in vitro, to restore normal myelination and neuron integrity, and thus to ameliorate CMT in animals in vivo. The results also show these combinations can protect animals from chemotherapy-induced or traumatic neuropathies. As a result, these compositions may be used to prevent or reduce chemotherapy-induced neuropathy, thereby allowing patients to receive chemotherapy for longer periods. Also illustrated in the experimental section are the nerve regeneration promoting properties of compositions of the invention. Indeed, the inventors have demonstrated a neurotrophic activity of the combinations of the invention which is characterized by a promotion of axon growth and of myelination, which results in a significant restoration of the transmission of nerve impulses to the muscle. Consequently, the compositions of the invention may be used to improve and/or accelerate recovery from any neuronal insult, either of genetic, chemical or mechanical origin (e.g., traumatic).

Another object of this invention is a composition comprising naltrexone, baclofen and a further distinct PMP22 inhibitor as defined above.

A further object of this invention is a composition as disclosed above further comprising one or several pharmaceutically acceptable excipients or carriers (i.e., a pharmaceutical composition).

Another object of this invention is a method of promoting nerve regeneration in a subject in need thereof, the method comprising administering to the subject an effective amount of a compound or a combination of compounds as disclosed above.

Another object of the present invention relates to a composition as disclosed above for treating CMT or a CMT related disorder.

A further object of this invention relates to the use of a combination of compounds as disclosed above for the manufacture of a medicament for the treatment of CMT or CMT a related disorder.

A further object of this invention is a method for treating CMT or a CMT related disorder, the method comprising administering to a subject in need thereof an effective amount of a composition as defined above.

A further object of this invention is a method of preparing a pharmaceutical composition, the method comprising mixing the above compounds in an appropriate excipient or carrier.

A more specific object of this invention is a method of treating CMT1A in a subject, the method comprising administering to the subject in need thereof an effective amount of a compound or combination of compounds as disclosed above.

A further specific object of this invention is a method of treating a toxic neuropathy in a subject, the method comprising administering to the subject in need thereof an effective amount of a compound or combination of compounds as disclosed above.

A further specific object of this invention is a method of treating ALS in a subject, the method comprising administering to the subject in need thereof an effective amount of a compound or combination of compounds as disclosed above.

A further specific object of this invention is a method of treating a traumatic neuropathy in a subject, the method comprising administering to the subject in need thereof an effective amount of a compound or combination of compounds as disclosed above.

In a particular embodiment, the subject in need of promoting nerve regeneration is suffering or has suffered from mechanical neuronal insults for instance traumatic brain injury, spinal cord injury, or injuries of peripheral nerves.

Another object of this invention is a method of improving and/or accelerating recovery from a neuronal insult in a subject in need thereof, the method comprising administering to the subject an effective amount of a compound or combination of compounds as disclosed above.

In a particular embodiment, the subject in need of improving and/or accelerate recovery from mechanical neuronal insult is suffering or has suffered from traumatic brain injury, spinal cord injury, or injuries of peripheral nerves.

Therapy according to the invention may be performed as drug combination and/or in conjunction with any other therapy. It and may be provided at home, the doctor's office, a clinic, a hospital's outpatient department, or a hospital, so that the doctor can observe the therapy's effects closely and make any adjustments that are needed.

The duration of the therapy depends on the stage of the disease being treated, the age and condition of the patient, and how the patient responds to the treatment.

Additionally, a person having a greater risk of developing an additional neuropathic disorder (e.g., a person who is genetically predisposed to or have, for example, diabetes, or is being under treatment for an oncological condition, etc.) may receive prophylactic treatment to alleviate or to delay eventual neuropathic response.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers both drugs.

Formulation of Pharmaceutical Compositions

The administration of each drug of the combination may be by any suitable means that results in a concentration of the drug that, combined with the other component, is able to ameliorate the patient condition (which may be determined e.g., in vitro by an effect on elevated expression of PMP22 upon reaching the peripheral nerves).

While it is possible for the active ingredients of the combination to be administered as the pure chemical, it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable and adapted for use for treatment with the combination of the present invention.

The drug may be contained in any appropriate amount in any suitable carrier substance, and may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

The drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug(s) into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally nontoxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The Emulsifying Agents May be Naturally Occurring Gums (e.g., Gum Acacia or Gum Tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering one of the active ingredients should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs that are subject of this invention can be used together for the preparation of a medicament useful for reducing the effect of increased expression of PMP22 gene; restoration of normal myelination and nerve integrity, preventing or reducing the risk of developing CMT disease, halting or slowing the progression of CMT disease once it has become clinically manifest, and preventing or reducing the risk of a first or subsequent occurrence of an neuropathic event.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration will be indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in the combination preferred for a unit dosage will depend upon several factors including the administration route, the body weight and the age of the patient, the severity of the neuropathic damage caused by CMT disease or risk of potential side effects considering the general health status of the person to be treated.

Additionally, pharmacogenomic (the effect of genotype on the pharmacokinetic, pharmacodynamic or efficacy profile of a therapeutic) information about a particular patient may affect the dosage used.

Except when responding to especially impairing CMT disease cases when higher dosages may be required, or when treating children when lower dosages should be chosen, the preferred dosage of each drug in the combination will usually lie within the range of doses not above the usually prescribed for long-term maintenance treatment or proven to be safe in the large phase 3 clinical studies.

For example, for rapamycin, from about 1 to about 100 µg/kg per day, typically from 1 to 50 µg/kg, for instance between 5 and 30 µg/kg/day.

for mifepristone, from about 1 to about 300 µg/kg per day, typically from 10 to 200 µg/kg, for instance between 10 and 80 µg/kg/day.

for naltrexone, from about 1 to about 100 µg/kg per day, typically from 1 to 50 µg/kg, for instance between 1 and 20 µg/kg/day.

for pilocarpine, from about 1 to about 100 µg/kg per day, typically from 1 to 50 µg/kg, for instance between 1 and 20 µg/kg/day.

for baclofen, from about 1 to about 300 µg/kg per day, typically from 10 to 200 µg/kg, for instance between 20 and 100 µg/kg/day.

for methimazole, from about 1 to about 100 µg/kg per day, typically from 1 to 50 µg/kg, for instance between 1 and 20 µg/kg/day.

for sorbitol, from about 17 µg/kg to about 17 mg/kg per day, typically from 167 µg/kg to 7 mg/kg per day, for instance between 333 µg/kg per day and 3.5 mg/kg per day.

Typically, administered doses correspond to those applied for a human of 60 kg.

The most preferred dosage will correspond to amounts from 1% up to 10% of those usually prescribed for long-term maintenance treatment.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

A. Preparation of Drug Combinations

The following drug combinations were prepared:

|  | Molecule | dose |
|---|---|---|
| Mix1 | sorbitol | 2.1 mg/kg/day |
|  | S-baclofen(−) | 60 µg/kg/day |
|  | naltrexone | 7 µg/kg/day |

|  | Molecule | dose |
|---|---|---|
| Mix2 | rapamycin | 15 µg/kg/day |
|  | mifepristone | 40 µg/kg/day |

|  | Molecule | dose |
|---|---|---|
| Mix3 | rapamycin | 15 µg/kg/day |
|  | mifepristone | 40 µg/kg/day |
|  | pilocarpine | 7 µg/kg/day |

|  | Molecule | dose |
|---|---|---|
| Mix4 | rapamycin | 15 µg/kg/day |
|  | mifepristone | 40 µg/kg/day |
|  | baclofen | 60 µg/kg/day |

|  | Molecule | dose |
|---|---|---|
| Mix5 | rapamycin | 15 µg/kg/day |
|  | mifepristone | 40 µg/kg/day |
|  | methimazole | 4.2 µg/kg/day |

|  | Molecule | dose |
|---|---|---|
| Mix6 | rapamycin | 15 µg/kg/day |
|  | naltrexone | 7 µg/kg/day |
|  | methimazole | 4.2 µg/kg/day |

|  | Molecule | dose 1 | dose 2 | dose 3 |
|---|---|---|---|---|
| Mix7 | sorbitol | 10.5 mg/kg/day | 2.1 mg/kg/day | 1.05 mg/kg/day |
|  | (RS) baclofen | 0.3 mg/kg/day | 60 µg/kg/day | 30 µg/kg/day |
|  | naltrexone | 35 µg/kg/day | 7 µg/kg/day | 3.5 µg/kg/day |

B. In Vitro Experiments

1. PMP22 Expression Assays on Schwann Cells Treated with Mix1-6

1.1 Cell Culture 1.1.1: Commercially Available Rat Primary Schwann Cells

Vials of rat Schwann cells (SC) primary culture (Sciencell #R1700) are defrost and seeded at the density of 10 000 cells/cm2 in "Sciencell Schwann cell medium" (basal medium from Sciencell #R1701) in poly-L-lysine pre-coated 75 cm$^2$ flasks. The culture medium is composed of basal medium, 5% Fetal Bovine Serum (3H-Biomedical AB #1701-0025), 1% Schwann cell growth supplement (3H Biomedical AB #1701-1752), 1% Gentamicin (Sigma #G1397) and 10 µM of Forskolin (Sigma #F6886) to promote their proliferation.

After reaching confluency (4 to 10 days depending on cell batch), Schwann cells are purified by gentle agitation or by thy1.1 immunopanning that allow SC isolation from adherent fibroblasts, to produce cultures that are at least 95% pure. SC are then counted (Tryptan blue method) and seeded in poly-L-lysine pre-coated 75 cm$^2$ flask in the same SC medium. At confluency, cells are rinsed, trypsinized (trypsin-EDTA 1× diluted from Invitrogen #1540054), diluted in PBS without calcium and magnesium) counted and platted in 12 well-dishes (140 000 cells/well) in Sciencell Schwann cell medium with 5% of FBS, 1% of cell growth supplement (CGS), 40 µg/ml of gentamicin and 4 µM Forskolin.

1.1.2 Custom-Made Rat Primary Schwann Cells

Primary Schwann cell cultures (SC) are established from Sprague-Dawley new-born rats (between P0 and P2) sciatic nerves. All new-born rats are sacrificed and isolated in a Petri dish. Dissection is performed under sterile conditions.

The dorsal skin is removed from the hind paw and the lower torso. The sciatic nerve is isolated and transferred to a culture dish containing ice-cold Leibovitz (L15, Invitrogen #11415) supplemented with 1% penicillin/streptomycin solution (50

UI/ml and 50 μg/ml, respectively; Invitrogen #15070) and 1% of bovine serum albumin (BSA, Sigma A6003). Both nerves per rats are transferred in a 15 ml tube containing ice-cold L15. The L15 medium is then removed and replaced by 2.4 ml of DMEM (Invitrogen #21969035) with 10 mg/ml of collagenase (Sigma #A6003). Nerves are incubated in this medium for 30 minutes at 37° C. The medium is then removed and both nerves are dissociated by trypsin (10% trypsin EDTA 10×, Invitrogen #15400054) diluted in PBS without calcium and magnesium (Invitrogen #2007-03) for 20 min at 37° C. The reaction is stopped by addition of DMEM containing DNase I grade II (0.1 mg/ml Roche diagnostic #104159) and foetal calf serum (FCS 10%, Invitrogen #10270). The cell suspension was triturated with a 10 ml pipette and passed through a filter in a 50 ml tube (Swinnex 13 mm filter units, Millipore, with 20 μm nylon-mesh filters, Fisher). The cell suspension is centrifuged at 350 g for 10 min at room temperature (RT) and the pellets are suspended in DMEM with 10% FCS and 1% penicillin/streptomycin. Cells are counted (Tryptan blue method) and seeded in Falcon 100 mm Primaria tissue culture plates at the density of $5\,10^5$ to $10^6$ cells/dish.

After one day of culture, the medium is changed with DMEM, 10% FCS, 1% penicillin/streptomycin and 10 μM of cytosine b-D-arabinofuranoside (Sigma #C1768). 48 hrs later, medium is eliminated and cells are washed three times with DMEM. The SC growth medium is then added, composed of DMEM, 10% FCS, 1% penicillin/streptomycin, 2 μM of Forskolin (Sigma #F6886), 10 μg/ml of bovine pituitary extract (PEX, Invitrogen #13028). The medium is replaced every 2-3 days.

After 8 days of culture (4 to 10 days depending on cell batches), Schwann cells reach confluency and the culture, containing a large amount of contaminating fibroblasts, is purified by the thy1.1 immunopanning method. After this purification, cells are suspended in growth medium at 10 000 cells/cm2 in poly-L-lysine pre-coated 75 cm² flasks. Once they reach confluency, cells are rinsed, trypsinized (trypsin-EDTA), counted and platted in 12 well-dishes (100 000 cells/well).

1.1.3 Drug Incubation

After cells being platted in 12 well-dishes, the medium is replaced by a defined medium consisting in a mix of DMEM-F12 (Invitrogen #21331020) complemented by 1% of N2 supplement (Invitrogen #17502), 1% L-Glutamine (Invitrogen #25030024) 2.5% FBS (Sciencell #0025), 0.02 μg/ml of corticosterone (Sigma #C2505), 4 μM Forskolin and 50 μg/ml of gentamycin. Growth factors are not added to this medium, to promote SC differentiation 24 hours later, the medium is replaced by a defined medium (DMEM-F12) complemented with 1% Insulin-Transferrin-Selenium—X (ITS, Invitrogen #51300), 16 μg/ml of Putrescine (Sigma #P5780), 0.02 μg/ml of corticosterone and 50 μg/ml of gentamicin. At this step, neither progesterone nor forskolin are present in the medium.

One day later, Schwann cells are stimulated by combinations of drugs during 24 hrs (3 wells/condition). The preparation of each compound is performed just prior to its addition to the cell culture medium.

Drugs are added to a defined medium composed of DMEM-F12, with 1% Insulin-Transferrin-Selenium—X (ITS, Invitrogen #51300), 16 μg/ml of Putrescine, 0.02 μg/ml of corticosterone, 10 nM Progesterone and 50 μg/ml of gentamicin. The absence of Forskolin during drug stimulation avoids adenylate cyclase saturation.

1.2. Schwann Cells Purification by Thy1.1 Immunopanning

To prevent fibroblast culture contamination, Schwann cells are purified using the clone Thy1.1 (ATCC TIB-103™) immunopanning protocol.

Antibody pre-coated 100 mm bacteria Petri dishes are prepared as follows: these dishes are washed three times with PBS and treated by 20 ml of Tris HCl solution 50 mM, pH 9.5, with 10 μg/ml of goat Anti-Mouse IgM MU antibody (Jackson ImmunoResearch #115-005-020) overnight at 4° C.; then rinsed 3 times with PBS and treated by a solution of PBS with 0.02% of BSA and supernatant obtained from T11D7e2 hybridoma culture (ATCC #TIB-103) containing the Thy1.1 IgM antibody for 2 hours at room temperature. Finally, the plates are washed three times with PBS before the cell suspensions are added.

SC are detached with trypsin EDTA. As soon as the majority of cells are in suspension, the trypsin is neutralized with DMEM-10% FBS and the cells are centrifuged. The pellet of dissociated cells is resuspended in 15 ml of medium with 0.02% BSA at the density of $0.66\times10^6$ cells per ml (maximum) and transferred to Petri dish (about 6.6 million of cells/10 ml/dish of 100 mm).

The cell suspension is incubated in the Thy 1.1 coated Petri dish during 45 min at 37° C. with gentle agitation every 15 min to prevent non-specific binding. The majority of fibroblast cells expressing Thy1.1 adhere on the dish. At the end of the incubation, the cell suspension is recovered and centrifuged. This cell suspension contains in theory only Schwann cells. Cells are centrifuged and cell pellet is suspended in growth medium with 10 μM of Forskolin at 16 000 cells/cm² in T75 cm² flask Poly-L-Lysine treated.

1.3 Quantitative Reverse Transcriptase Polymerase Chain Reaction (Q-RT-PCR)

Quantitative RT-PCR is used to compare the levels of PMP22 mRNA after drug stimulation, relative with housekeeping Ribosomal L13A mRNA in rat Schwann cell primary culture.

After rinsing with cold sterilized PBS, total RNAs from each cell sample are extracted and purified from SC using the Qiagen RNeasy micro kit (Qiagen #74004). Nucleic acids are quantified by Nanodrop spectrophotometer using 1 μl of RNA sample. The RNA integrity is determined through a BioAnalyzer (Agilent) apparatus.

RNAs are reverse-transcribed into cDNA according to standard protocol. cDNA templates for PCR amplification are synthesized from 200 ng of total RNA using SuperScript II reverse-transcriptase (Invitrogen #18064-014) for 60 min at 42° C. in the presence of oligo(dT), in a final volume of 20 μl.

cDNAs are subjected to PCR amplification using the <<LightCycler® 480>> system (Roche Molecular Systems Inc.) Each cDNA are diluted five times before being used for PCR amplification. 2.5 μl of this cDNAs enters the PCR reaction solution (final volume of 10 μl). Preliminary experiments ensured that quantitation was done in the exponential phase of the amplification process for both sequences and that expression of the reference gene was uniform in the different culture conditions.

PCR reaction is performed by amplification of 500 nM of forward primer of rat PMP22 (NM_017037), 5-GGAAACGCGAATGAGGC-3 (SEQ ID NO: 1), and 500 nM of reverse primer 5-GTTCTGTTTGGTTTGGCTT-3 (SEQ ID NO: 2) (amplification of 148-bp). A 152-bp fragment of the RPL13A ribosomal (NM_173340) RNA is amplified in parallel in separate reactions for normalization of the results by using a 500 nM of forward primer 5-CTGCCCT- CAAGGTTGTG-3 (SEQ ID NO: 3), and a 500 nM of reverse primer 5-CTTCTTCTTCCGGTAATGGAT-3 (SEQ ID NO: 4).

We used FRET chemistry to perform RT-Q-PCR analysis. FRET probes are composed of 0.3 µM of Pmp22-FL-5-GCTCTGAGCGTGCATAGGGTAC (SEQ ID NO: 5) or Rpl13A-FL-5-TCGGGTGGAAGTACCAGCC (SEQ ID NO: 6), labelled at their 3' end with a donor fluorophore dye (Fluorescein). 0.15 µM Red640 probes are defined as follows: Pmp22-red-5'-AGGGAGGGAGGAAGGAAACCAGAAA (SEQ ID NO: 7) or Rpl13A-red-5'-TGACAGCTACTCTG-GAGGAGAAACGGAA (SEQ ID NO: 8), labelled at their 5' end with an acceptor fluorophore dye (Rhodamine Red 640).

Each PCR reaction contained 2.5 µl cDNA template in a final volume of 10 µl of master mix kit (Roche #04-887301001).

The following PCR conditions are used: 10 sec at 95° C., 10 sec at 63° C. and 12 sec at 72° C. and 30 sec at 40° C. (Forty amplification cycles). The relative levels of PMP22 gene expression is measured by determining the ratio between the products generated from the target gene PMP22 and the endogenous internal standard RPL13A.

1.4 PMP22 Protein Expression Analysis by Flow Cytometry (FACS)

8 hrs, 24 hrs and 48 hrs after drugs incubation, supernatants are recovered, centrifuged and frozen. SC are detached with trypsin-EDTA. As soon as the majority of cells are in suspension, the trypsin is neutralised using DMEM with 10% FCS.

Supernatants with cells are recovered and centrifuged. The pellets of cells are transferred in micro tubes, washed in PBS once and fixed with a specific solution (AbCys #Reagent A BUF09B). 10 minutes later, cells are rinsed once with PBS and kept at 4° C.

Five days after cell fixation, all cell preparations with different incubation times are labelled using the following protocol.

Cells are centrifuged at 7000 rpm for 5 minutes and the pellets are suspended in a solution of permeabilization (AbCys #Reagent B BUF09B) and labelled with primary PMP22 antibody (Abcam #ab61220, 1/50) for 1 hr room at temperature. Cells are then centrifuged at 7000 rpm for 5 minutes and cell pellets are rinsed once in PBS. A secondary antibody is added, coupled to Alexa Fluor 488 (goat anti-rabbit IgG, Molecular Probes #A11008, 1/100), for one hour at room temperature. Cells are then centrifuged at 7000 rpm for 5 minutes and cell pellets are rinsed once in PBS. The labelling is increased adding a tertiary antibody coupled to Alexa Fluor 488 (chicken anti-goat IgG, Molecular Probes #A21467, 1/100) for one hour incubation, at room temperature. Cells are then rinsed once in PBS. Control without any antibody (unlabelled cells) is performed to determine the level of auto fluorescence and adapted the sensitivity of the photomultiplicators. Control with both secondary and tertiary antibodies but without primary antibody, is performed to assess nonspecific binding of antibodies.

Data acquisition and analysis are performed with a FACS Array cytometer and FACS Array software (Becton Dickinson) on 5000 cells. Forward Scatter (FSC) correlated with cell volume (size) and Side Scatter (SSC) depending on inner complexity of cells (granularity) are analysed. For expression of PMP22, analysis is performed within the total cells and percent of positive cells is calculated. Positive cells are cells with fluorescence intensity higher than the control with secondary antibody.

In order to quantify the number of SC, cells in control medium are analysed using antibodies anti-S100 Protein.

Cells are prepared according to the following protocol: Schwann cells are stained with antibody anti-S100 Protein (Dako #S0311, 1/100) for 1 hr room at temperature. This antibody is labelled according to protocol described above for PMP22 immunostaining but without incubation with tertiary antibody.

1.5. Drug Incubation and Activity

Drugs are incubated for 24 hrs or 48 hrs in the same defined medium than described above (3 wells/condition) in absence of Forskolin to avoid adenylate cyclase stimulation saturation, but in presence of 10 nM of progesterone. After drug incubation, supernatants are recovered and Schwann cells are frozen for RT-Q-PCR analysis.

These experiments are summarized in Table 1.

TABLE 1

| Combination | PMP22 expression |
|---|---|
| Mix1 | down regulation |
| Mix2 | down regulation |
| Mix3 | down regulation |
| Mix4 | down regulation |
| Mix5 | down regulation |
| Mix6 | down regulation |

2. Assessment of Synergistic Effect of Compounds in Mix7 in a Co-Culture Model for CMT A model of co-culture was used as an in vitro model of CMT1A. This model of myelination consists in co-culturing sensory neurons and Schwann cells from male PMP22 Transgenic (TG) dissociated Dorsal Root Ganglia (DRG).

The aim of this study is to assess the effect of 3 test compounds (+/−baclofen, naltrexone and sorbitol) and Mix7 (a mixture of these 3 drugs) on myelination process. The effect of the 3 test compounds, and their mixture on myelination, are assessed by evaluating Myelin Basic Protein (MBP) expression in presence of ascorbic acid.

2.1 Materials and Methods

Fifteen days gestation pregnant female rats are killed by cervical dislocation. The embryos are removed from the uterus and are at similar fetal stage of development.

2.1.1 Genotyping

A piece of each embryo head (3 mm$^3$) is placed in a 2 ml tube DNase free. The DNA is extracted with the SYBR Green Extract-N-Amp tissue PCR kit (Sigma, ref XNATG-1KT). One hundred and twenty µl of extraction solution (Kit Sigma, ref XNATG-1KT) was put on each piece of embryo head. The heads are incubated for 10 min at room temperature. At the end of this incubation, the heads are incubated for 5 min at 95° C. in the extraction solution. Immediately after this last incubation, 100 µl of neutralizing solution are added, each DNA extract is diluted at 1/40 with sterile ultrapure water (Biosolve, ref: 91589) and stored at +4° C. until use. The genotyping of female (F) and male (M) embryos is performed during the dissection of the DRG, with the kit Fast SYBR Green Master Mix (Applied Biosystem, 4385612). The gender of each embryo is determined using the male SRY gene. The SRY primers are supplied by Pharnext (SRY-F (SEQ ID NO: 9): 5'-GAGAGAGGCACAAGTTGGC-3; SRY-R (SEQ ID NO: 10): 5'-GCCTCCTGGAAAAAGGGCC-3'). SRY primers are diluted at 3 µM in sterile ultrapure water (Biosolve, ref: 91589). A mix for PCR is prepared with ultrapure water (4 µl per sample), primer at 3 µM (2 µl per sample) and Master Mix (10 µl per sample). In a PCR 96 wells plate, 16 µl of PCR mix is deposited in each well. Four µl of each diluted DNA is added according to a plan deposit. The PCR is run using the 7500 fast RT-PCR system (Applied Biosystem), with the following program:

Beginning 95° C.-20 sec 45 cycles: 95° C.-10 sec, 65° C.-10 sec, 72° C.-30 sec (data acquisition).

Melt curve: 95° C.-15 sec, 64° C.-1 min, 90° C.-30 sec (continuous data acquisition), 60° C. 15 sec. The amplification plots and melt curves are analyzed with the 7500 software (Applied Biosystems).

2.1.3. Drug Incubation

On day 7, the following test compounds (alone or in combination) are added in the medium with 50 μg/ml ascorbic acid:

(RS)-baclofen naltrexone

D-sorbitol

Mix7=the combination of the 3 individual compounds.

These compounds or compound combination are tested at the following concentrations (Table 2):

TABLE 2

Concentration of individual drugs or in combination used for in vitro studies of MBP expression in TG DRG/SC co-cultures.

|  |  | Dose 1 | Dose 2 | Dose 3 | Dose 4 | Dose 5 | Dose 6 | Dose 7 |
|---|---|---|---|---|---|---|---|---|
| Individual drugs | naltrexone | 5 μM | 1 μM | 200 nM | 40 nM | 8 nM | 1.6 nM | 320 pM |
|  | D-sorbitol | 500 μM | 100 μM | 20 μM | 4 μM | 800 nM | 160 nM | 32 nM |
|  | (RS)-baclofen | 5 μM | 1 μM | 200 nM | 40 nM | 8 nM | 1.6 nM | 320 pM |
| Mix7 | naltrexone | 5 μM | 1 μM | 200 nM | 40 nM | 8 nM | 1.6 nM | 320 pM |
|  | D-sorbitol | 500 μM | 100 μM | 20 μM | 4 μM | 800 nM | 160 nM | 32 nM |
|  | (RS)-baclofen | 5 μM | 1 μM | 200 nM | 40 nM | 8 nM | 1.6 nM | 320 pM |

The results for each sample are compared to negative control (ultrapure water) and to the positive control (TG/Male and WT/Female), to conclude on the genotype of each embryo.

2.1.2 Sensory Neurons and Schwann Cells Co-Cultures

Rat Dorsal root ganglions are cultured as previously described by Cosgaya et al., 2002 and Rangaraju et al., 2008.

Each embryo is dispatched on numerating petri dish (35 mm of diameter). The head of embryo is cut, placed on 1.5 ml tube DNAase free; the ADN is extracted with the Extract-N-Amp Tissue Kit (Sigma Aldrich). The genotyping (Male (M) and female (F), wild type and PMP22 transgenic) is performed with the kit Fast SYBR Green Master Mix (Applied Biosystem). This genotyping is performed in parallel of the dissection of dorsal root ganglia (DRG), so that at the end of the dissection, only one type of culture (DRG from transgenic male) is done. DRG of each embryo is collected, placed in ice-cold medium of Leibovitz (L15, Invitrogen). At the end of the dissection, DRG of TGM are pooled and dissociated by trypsinization (trypsin EDTA, 0.05%; Invitrogen) for 20 min at 37° C. The reaction is stopped by addition of DMEM containing 10% of fetal bovine serum (FBS) in the presence of DNAase I (Roche). The suspension is triturated with a 10 ml pipette. Cells are then centrifuged at 350×g for 10 min at room temperature. The pellet of dissociated cells is resuspended in neurobasal medium (Invitrogen) containing 2% of B27 (Invitrogen), 1% of penicillin-streptomycin (Invitrogen), 1% de L glutamine and 50 ng/ml NGF (Sigma). This medium is the neuronal medium. Viable cells are counted in a Neubauer cytometer using the trypan blue exclusion test (Sigma) and seeded on the basis of 10 000 cells per well in 96 well-plates (Greiner) treated with poly-L-lysine. The plates are maintained at 37° C. in a humidified incubator, in an atmosphere of air (95%)-CO2 (5%). Half of the standard neuronal culture medium is changed every other day. The cultures are maintained in standard neurobasal medium for 7 days to allow Schwann cells to populate the sensory neuron neurites. On day 7, the cultures are fed with standard neuronal medium supplemented or not with 50 μg/ml ascorbic acid in order to initiate basal lamina formation and myelination.

The test compounds are incubated for 5 different times: 5, 9, 10, 11 and 13 days.

Three separate and independent cultures of DRG (from TG embryos male rats) are done. These conditions are assessed in presence of ascorbic acid, 6 wells per condition. The solution ready to use of all test compounds are extemporaneously prepared from a stock solution, stored at −20° C. This solution is prepared once a week. Half of the standard neuronal medium supplemented with test compounds and ascorbic acid (each at the concentration 1×) are changed every other day.

2.1.4 Staining Protocol

After 5, 9, 10, 11 and 13 days of incubation, cells are fixed by a cold solution of ethanol (95%) and acetic acid (5%) for 10 min. The cells are permeabilized and blocked with PBS containing 0.1% saponin and 10% goat serum for 15 min. Then, the cells are incubated with a specific marker of myelin: polyclonal antibody anti-myelin basic protein (MBP) antibody (Sigma 118K0431).

This antibody is revealed with Alexa Fluor 568 goat anti-rabbit IgG and Alexa Fluor 488 goat anti-mouse IgG (Molecular probe 687621, 623962). Nuclei of neurons are labeled by a fluorescent marker (Hoechst solution, SIGMA ref B1155).

2.1.5. Data Processing

Per well, 20 pictures are taken using InCell Analyzer™ 1000 (GE Healthcare) with 20× magnification. All images are taken in the same conditions. Analysis of total length of myelinated axons was automatically done (length and area around axons) using Developer software (GE Healthcare). All values will be expressed as mean+/−s.e.mean. Statistical analyses are done on different conditions (ANOVA followed by Fisher's PLSD test when allowed).

2.2. Results

Synergistic Effect of Drugs in the Efficacy of Mix7

Figure 2A:
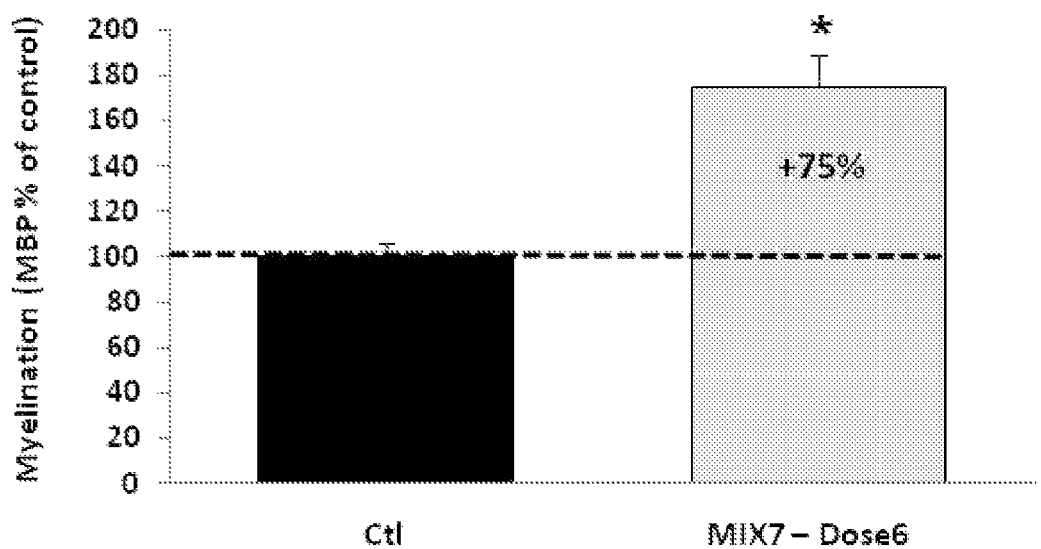
Figure 2B:
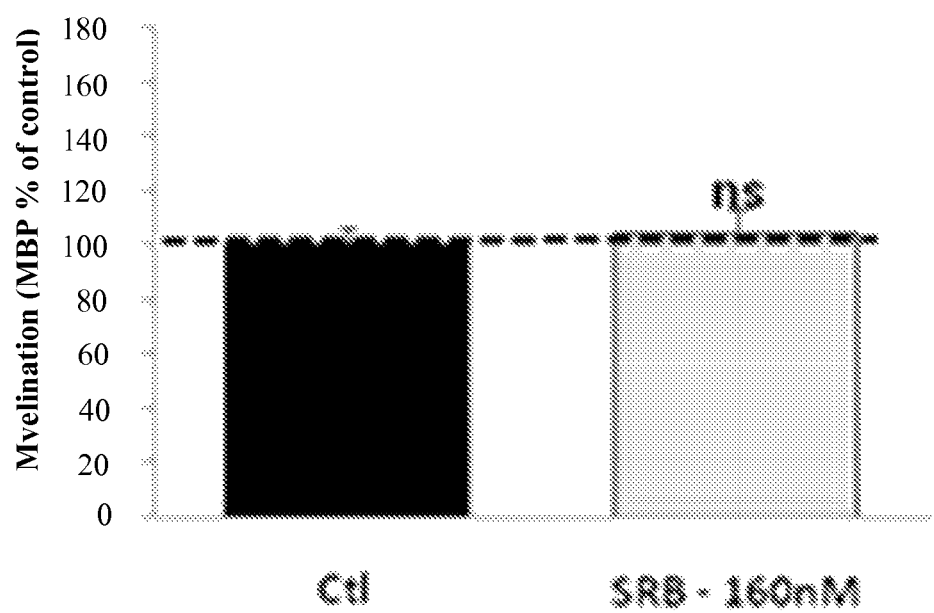
Figure 2C:
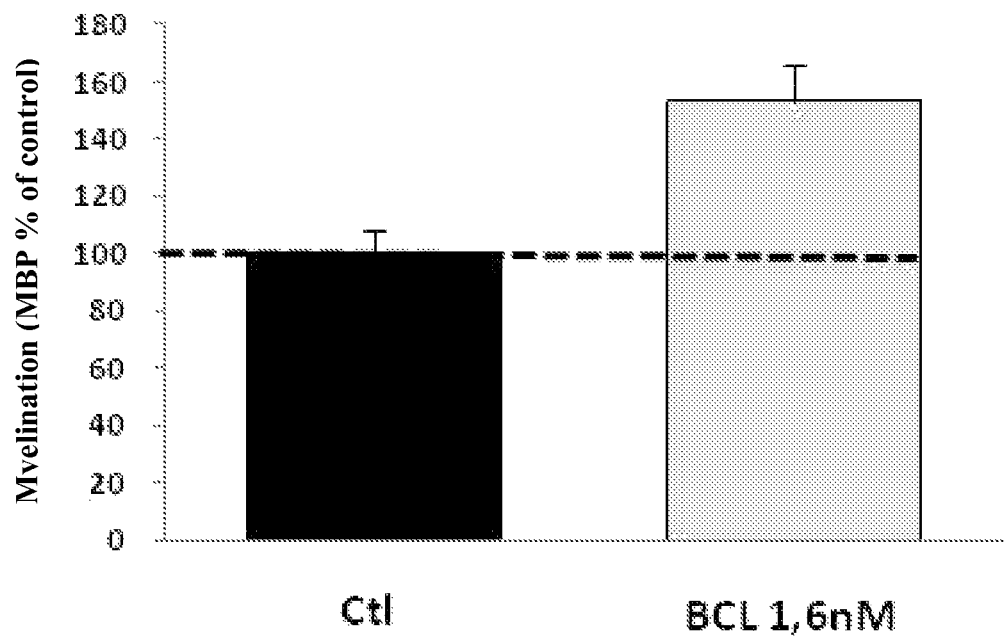
Figure 2D:
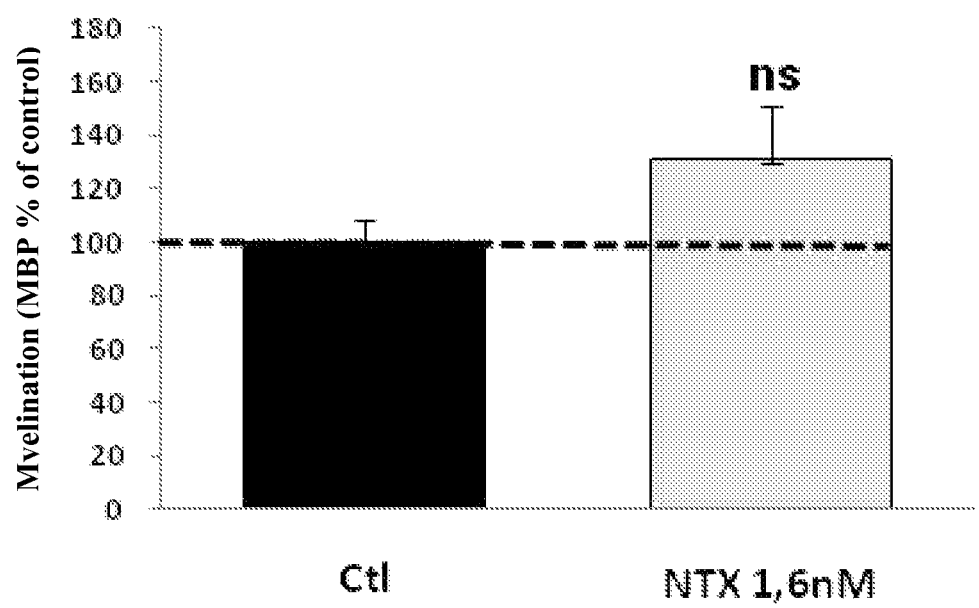

An important synergistic effect of drugs composing the Mix7 combination is observed on MBP expression. Indeed, on day 10 (=17 days of culture), combination of (RS)-baclofen, naltrexone and D-sorbitol significantly increases MBP expression at doses 1 and 6 as shown in FIGS. 1A and 2A. By contrast, the above drugs used individually have no substantial effect compared to control (FIGS. 1B-D and 2B-D).

A significant effect on MBP expression is also recorded after 10 days of incubation at doses 2, 3, 4, 5 and 7 of Mix7 (FIG. 3A).

This effect is still observed on day 11 with doses 2-7 (FIG. 3B) in form of a clear bell shape curve.

C. Experiments In Vivo in CMT Animal Model

We tested the compounds for therapeutic effect in a rat model.

The experimental groups are formed with young rats of both genders separately. The rats are assigned to the groups following randomization schedule based on the body weight. In some experiments the randomization is based on the performances of the rats in the bar test. Both genders are represented by separate control groups that are numerically equal or bigger than the treatment groups.

The rats are treated chronically with drugs—force fed or injected by Alzet osmotic subcutaneous pump (DURECT Corporation Cupertino, Calif.), depending on each drug bioavailability during 3 or 6 weeks. In all the in vivo experiments performed, the Mix7 is administered by gavage.

The animals are weighted twice a week in order to adjust the doses to growing body weight. If the osmotic pump is chosen for the treatment administration, the doses of the drug are calculated on the basis of the estimated mean body weight of the animals expected for their age over the period of the pump duration (6 weeks). The pumps are re-implanted if necessary, with the appropriated anesthesia protocol.

Behavioural Tests

Each three or four weeks the animals are subjected to a behavioural test. Each test is conducted by the same investigator in the same room and at the same time of the day; this homogeneity is maintained throughout entire experiment. All treatments and genotype determination are blinded for the investigator. "Bar test" and "Grip strength" has been mainly used to access the performance throughout study. The schedule of the bar test may change as the animal growth (in order to avoid the bias due to the learning, for example).

The assay of the grip strength allows detection of subtle differences in the grip performance that seems to be composed of the muscle force, sensitivity status (for instance, painful tactile feelings may change measured values of the force), behavioural component ("motivation"). The values differ between fore and hind limbs and greatly depend on the age of the animals.

The grip strength test measures the strength with which an animal holds on to a grip with its forepaws or its hindpaws separately. A dynamometer is placed with a grip to measure the strength (Force Gauge FG-5000A). The rat is held by the experimenter in a way that it grasps the grip either with its forepaws or with its hind paws and pulls gently the rat backwards until it releases the grip. The force measured when the animal releases the grip is recorded.

Two successive trials measuring the forepaws and two successive trials measuring the hindpaws strength per animal are processed; only the maximum score (one for forepaws and one for hindpaws) is noticed (in N).

The Bar Test

The bar test evaluates rats' ability to hold on a fix rod. Pmp22 rats which display muscular weakness, exhibit a performance deficit in this test (Sereda et al, 1996). The rat is placed on its four paws on the middle of the rod (diameter: 2.5 cm; length: 50 cm; 30 cm above the table). Trials are performed consecutively; the number and the duration of trials in our experiments have been depending on batches of the animals. This variability in the testing has been introduced in order to determine the schedule appropriated to the best detection of the motor deficiency in the CMT rats in the course of the experiments.

Performance indices are recorded on each session:

The number of trials needed to hold for 60 sec (or 30 sec for batch 1, session 1 and 2) on the rod.

The time spent on the bar (i.e. the fall latency) in each trial and the average on the session. In the experimental procedures where the session ends after the rat has stayed for a cut-off time, i.e. 30 or 60 s, on the bar, a performance of the cut-off time (30 s or 60 s) is assigned to trials not completed (e.g.: for batch 8, for an animal which stays on the bar less than 10 sec on trials 1, 2 and 3, then for 60 sec on trials 4 and 5, 60 s is assigned to trials 6 to 10).

The number of falls.

General Health Assessment

Body weights, overt signs (coat appearance, body posture, gait, tremor etc.) of the animals are monitored throughout the experiment. The rating scale is used for recording: 0=normal, 1=abnormal.

The Gait

Each rat is observed in a novel rat cage (dimensions 55×33×18 cm) without litter for five minutes. The gait of rats is evaluated with 4 parameters:

Score 0: normal gait (fluid)

Score 1: abnormal gait (not fluid or the rat has a slight limp)

Score 2: moderate incapacity (the rat drags one's leg and is able to put it right and walk)

Score 3: serious incapacity (the rat drags its one's or both hindpaws but is unable to put it/them right).

Inclined Plane Test

The sliding apparatus had a 30×50 cm Plexiglas plane that could be inclined at an angle of 0° (horizontal) to 60°. Each rat was initially placed on the 25°-angled inclined plane in the up-headed position (head-up orientation); two trials separated by 1 min are performed. 30 min later, the same experiment is realized on a 35°-angled inclined plane then on 40°-angled inclined plane. During this time the rat was returned to its cage. The plane is cleaned after each trial.

The performances of rats are evaluated by 4 different scores:

Score 0: no slide

Score 1: a little slide (one or two paws)

Score 2: a moderate slide (4 paws) but not until the end of the plane

Score 3: the rat is sliding until the very bottom of the plane.

Further Tests

When appropriate, the rats are subjected to electrophysiological evaluation, histological measurement and the pmp22 RNA expression level in the sciatic nerve is quantified.

Quantification of Pmp22 RNA in Sciatic Nerve by Quantitative RT-PCR

Total RNA was isolated from left sciatic nerves using Qiazol (ref No. 79306, Qiagen Gmbh, Germany) followed by the single-step purification method with RNeasy Mini Kit (ref No. 74106, Qiagen Gmbh, Germany) described by the manufacturer's protocol (Qiagen-RNeasy Fibrous tissue Handbook). DNA contamination was removed by digestion with RNase-free DNase I by use of the DNA-free kit (Qiagen-Rnase-free DNase set 1500 Kunitz units, ref No. 1023460).

RNA concentrations are estimated by NanoDrop ND-1000 and a test of quality control was done by Agilent RNA 6000 nano chips on Agilent 2100 Bioanalyzer.

Reverse transcription and real-time PCR: Quantitative RT-PCR (RT-Q-PCR) was performed as follows: 80 ng of total RNA was reverse transcribed using SuperScript™ II Reverse Transcriptase (Invitrogen, Carlsbad, Calif.) with Oligo(dT) 12-18 (Invitrogen, Carlsbad, Calif.) in a 20-μl reaction volume.

Real-time PCR was performed with a rapid thermal cycler system (LightCycler® 480 II, 384-Well, Roche, Switzerland). Amplifications are performed in a 10 μl total volume with primers concentration optimized between 130 nM and 1 μM. Primers and template are supplemented with LightCycler® 480 SYBR Green I Master (2× conc. Roche, Cat. Ref No. 04 887 352 001). Nucleotides, $MgCL_2$, Taq DNA polymerase and buffer are included in the mix. An amplification protocol incorporated an initial incubation at 95° C. for 10 min for the activation of Taq DNA polymerase followed by 45 cycles, with a 95° C. denaturation for 10 s, 60° C. annealing for 40 s and 72° C. extension for 10 s (detection of the fluorescent product was performed at the end of the 72° C. extension period by a single acquisition mode) and ended by a cycle of melting curve with 95° C. denaturation for 5 s, 63° C. annealing for 60 s and 95° C. (from 63° C. to 95° C. the ramp rate is 0.11° C./s and detection of the fluorescent product was continuous). To confirm the amplification specificity, the PCR product from each primer pair was subjected to a melting curve analysis. Relative quantification was performed based on the crossing point (Cp value) for each of the PCR samples. The point at which the fluorescence of a sample rises above the background fluorescence is called the "crossing point (Cp) of the sample. *Rattus norvegicus* Myelin Protein Zero (MPZ) gene was used for normalization (Sereda et al., 2006). The sequences of the primers (synthesized by Eurofins MWG Operon, Germany) used for the RT-Q-PCR analysis are:

```
                            (SEQ ID NO: 11)
PMP22 - forward:  5'-TGTACCACATCCGCCTTGG-3'
and (SEQ ID NO: 12)
PMP22 - reverse:  5'-GAGCTGGCAGAAGAACAGGAAC-3'.

(SEQ ID NO: 13)
MPZ-forward:      5'-TGTTGCTGCTGTTGCTCTTC-3'
and (SEQ ID NO: 14)
MPZ-reverse:      5'-TTGTGAAATTTCCCCTTCTCC-3'.
```

Results

Mix1 composition improves bar test performances throughout the treatment procedure (FIG. 4).

Mix1 improves the gait score of transgenic rats after 3 and 6 weeks of treatment as shown in FIG. 5.

Mix1 increases the performances of transgenic rats after 3, 6, 9 and 12 weeks of treatment in the inclined plane test at 25° described in the FIG. 6.

FIG. 7 illustrates the positive effect of Mix2 on gait score of transgenic rats at 25, 35 and 40° in the inclined plane test.

Mix7 (dose 3) significantly decreases the pmp22 RNA gene expression in the sciatic nerve of pmp22 transgenic rats (FIG. 9).

The performances of pmp22 rats treated with Mix7 (dose 2 and dose 3) are improved in the inclined plane test at 35° (FIG. 10). More specifically, 29 and 33% of rats belong to the good performance group, compared to 5% for TG placebo group, and 29 and 11% of rats belong to the poor performance group compared to 60% for the TG placebo group. P-value (versus the TG placebo) is equal to 0.0152 for the TG rats treated with Mix7-dose 2 and p-value is equal to 0.002 for the TG rats treated with Mix7-dose 3 versus the TG placebo).

Mix7-dose 3 significantly increases the fall latency time of pmp22 rats in bar test after 9 weeks of treatment (FIG. 11): black dashed line, p=4.56 10-2, n=18. Significant difference between TG placebo rats (black plain line, n=20) and WT placebo rats (grey plain line, p=3.82 10-7, n=18) is also observed.

The FIG. 12 illustrates the improvement of grip strength of the pmp22 rats treated with the Mix7-dose 3.

The FIG. 13 shows the significant correlation between the bar test latency time (after 9 weeks of treatment with the Mix7-dose 3) and the expression level of pmp22 RNA.

The FIG. 14 displays the significant correlation between the bar test latency time after 9 weeks of treatment with Mix7-dose 3 and the conduction velocity of the sensitive nerve (tail).

Similar results are obtained for other combinations (see Table 3).

TABLE 3

| Combination | PMP22 rat disease phenotype |
| --- | --- |
| Mix1 | improvement |
| Mix2 | improvement |
| Mix3 | improvement |
| Mix4 | improvement |
| Mix5 | improvement |
| Mix6 | improvement |

These data show that, in vivo, the combinations and regimens of this invention allow effective treatment of CMT.

D. In Vivo Effect in a Model of Toxic Neuropathy

The drug treatments or regimens are orally administered from the day before the first intraperitoneal injection of oxaliplatin 3 mg/kg (D −1) until the day before the last testing day (D16). Animals belonging to the oxaliplatin-treated group are dosed daily with distilled water (10 ml/kg). Animals are dosed with the tested treatment and distilled water daily during the morning whereas oxaliplatin is administered on the afternoon.

During the testing days (i.e. D1, D4, D10), the treatment and distilled water are administered after the test. Regarding the testing day (D4), including compounds and vehicle administrations and oxaliplatin injection, the treatment and distilled water are administered prior to the injection of oxaliplatin after the test. Animals from the reference-treated group are dosed only during the testing days (i.e. D1, D4, D10 and D17).

Cold allodynia is assessed by measuring the responses to thermal non-nociceptive stimulation (acetone test) on D1 (around 24 h after the first injection of oxaliplatin 3 mg/kg (acute effect of oxaliplatin), on D4, D10 and (chronic effect of oxaliplatin) and on D17 (residual effect of oxaliplatin one week after completion of treatment).

Testing is done using the acetone test 2 h post-administration of the reference. The reference substance is gabapentin, 100 mg/kg, per os (once a day×4 testing days).

Acetone Test

Cold allodynia is assessed using the acetone test. In this test, latency of hindpaw withdrawal is measured after application of a drop of acetone to the plantar surface of both hindpaws (reaction time) and the intensity of the response is scored (cold score).

Reaction time to the cooling effect of acetone is measured within 20 sec (cut-off) after acetone application. Responses to acetone are also graded to the following 4-point scale: 0 (no response); 1 (quick withdrawal, flick of the paw); 2 (prolonged withdrawal or marked flicking of the paw); 3 (repeated flicking of the paw with licking or biting).

Six trials by rat are performed. For each experimental group, the results are expressed as the cumulative cold score defined as the sum of the 6 scores for each rat together ±SEM. The minimum score being 0 (no response to any of the 6 trials) and the maximum possible score being 18 (repeated flicking and licking or biting of paws on each of the six trials).

gabapentin source: Zhejiang Chiral Medicine Chemicals, China oxaliplatin_source: Sigma, France The results are depicted on FIG. 8. They clearly show a protective effect of the composition of this invention on oxaliplatin-induced neuropathy.

E. In Vivo Effect in a Model of ALS

Animal Model

We have chosen the $SOD1^{G93A}$ rat model (generated by Howland et al) to mimic the Amyotrophic Lateral Sclerosis pathology. This model overexpresses the mutated SOD1 gene in spinal cord, many brain regions as well as peripheral tissues. The onset of the motor neuron disease of this model is about at 115 days; it appears as hind limb abnormal gait. In few days, the paralysis of hind limb arises.

Experimental Procedures

We obtained colonies by crossing breeder $SOD1^{G93A}$ rats with Sprague Dawley female rats. Heterozygous $SOD1^{G93A}$ rats are identified with polymerase chain reaction (PCR) of tail DNA with primers specific for hSOD1 [1]. Animals are maintained in a room with controlled illumination (lights on 0500-1900 h) and temperature (23±1° C.), and given free access to food and water. All the animal procedures in the present study are carried out in accordance with the guidelines standards of animal care.

Body weight measurement was performed every week and behavioural tests began at an age of 60 days and continued until endpoint. The treatments are administered every day per oral or subcutaneous way from the age of 5 weeks.

1. Observation Test: Characterization of the General Aspect

Each rat was observed in a novel rat cage (dimensions 55×33×18 cm) without litter for five minutes. Five different parameters are recorded:

The Gait
  score 0: normal gait (fluid)
  score 1: abnormal gait (not fluid or the rat has a slight limp)
  score 2: moderate incapacity (the rat drags one's leg and is able to put it right and walk)
  score 3: serious incapacity (the rat drags its one's or both hindpaws but is unable to put it/them right)
The Coat Aspect
  score 0: clean and silky coat
  score 1: piloerection or dirty coat
The Tremor
  score 0: no tremor
  score 1: tremor
The Body Position
  score 0: normal
  score 1: abnormal (flattened or arching its back)
The Hindpaws Position
  score 0: normal
  score 1: spread hindpaws 2. The Motor Score Test: Characterization of the Motor Deficit This test evaluates the ability of rats to right themselves within 30 sec of being turned on either side (righting reflex) (Gale et al.).

A non-parametrical scoring system was used following these criteria (Matsumoto et al., Thonhoff et al.):
  score 0: the rat is unable to right itself from either side within 30 sec
  score 1: the rat is unable to right itself from only one side within 30 sec
  score 2: the rat is able to right itself from both sides within 30 sec but is unable to stand in the cage; it is always dragging some parts of body
  score 3: the rat is able to right itself from both sides within 30 sec, is unable to stand in the cage but is not dragging some parts of body
  score 4: the rat is able to right itself from both sides within 30 sec, is able to stand in the cage but has visible functional deficits
  score 5: the rat is able to right itself from both sides within 30 sec, is able to stand in the cage and no visible functional deficits.

The end-point of disease is fixed at score 0; the rat is then euthanized.

3. Inclined Plane Test: Characterization of the Motor Deficit

The sliding apparatus had a 30×50 cm plexiglas plane that could be inclined at an angle of 0° (horizontal) to 60°. Each rat was initially placed on the 25°-angled inclined plane in the up-headed position (head-up orientation); two trials separated by 1 min are performed. 30 min later, the same experiment is realized on a 35°-angled inclined plane then on 40°-angled inclined plane. During this time the rat was returned to its cage. The plane is cleaned after each trial.

The performances of rats are evaluated by 4 different scores:
  score 0: no slide
  score 1: a little slide (one or two paws)
  score 2: a moderate slide (4 paws) but not until the end of the plane
  score 3: the rat is sliding until the very bottom of the plane.

4. The Wire Mesh Test: Characterization of the Motor Ability in Difficult Situation A wire mesh was placed in contact with a box at the top (at an angle of 70°) and the edge of a table at the bottom. Each rat was placed on the bottom of the wire mesh and motivated to ascend by placing their littermates in the box at the top. Each rat was trained once a week (3 trials).

The recorded parameter was the latency time to reach the top of the wire mesh.

5. The Open Field Test: Characterization of the Locomotor Activity

The locomotor activity was measured in a Plexiglas box (45×45×30 cm, Acti-Track by BIOSEB, Lyon, France) with 16 photo-cell beams following the two axes, 1 and 5 cm above the floor.

The spontaneous and exploratory activity of each rat was evaluated during 3 hours.

4 parameters are recorded (the total traveled distance, the number of rearings, the percentage of traveled distance and of time spent in the center of the open field).

F. In Vivo Effect in a Model of Mechanical Neuronal Insults-Sciatic Nerve Crush

Sciatic nerve crush is widely accepted as a valid model for the assessment of nerve regeneration. In this model, nerve damage results in a rapid disruption of nerve function as evidenced by the measure of the evoked muscle action potentials (CMAPs) generated through the stimulation of the injured sciatic nerve.

Nerve injury is characterized by a lower nerve conduction of the signal that results in an increased latency in generation of CMAP and in an impaired strength of action potential resulting in a decreased amplitude and duration.

1. Nerve crush

CD-1 mice (Charles River, non-diseased animals) were anesthetized using isoflurane (2.5-3% in air). The right thigh was shaved and the sciatic nerve was exposed at mid-thigh level (5 mm proximal to the bifurcation of the sciatic nerve) and crushed for 10 s twice with a microforceps (Holtex, P35311) with a 90° rotation between each crush. For sham operated animals, sciatic nerves were exposed but not crushed. Finally, the skin incision was secured with wound clips. First administration of Mix7-dose 3 was performed 30 min after the crush. From the day 1 to day 42, administration was performed once daily. On test days, mice were treated (10 ml/kg) 1.5 h before CMAP recording.

2. Electrophysiological Measures

Figure 15:
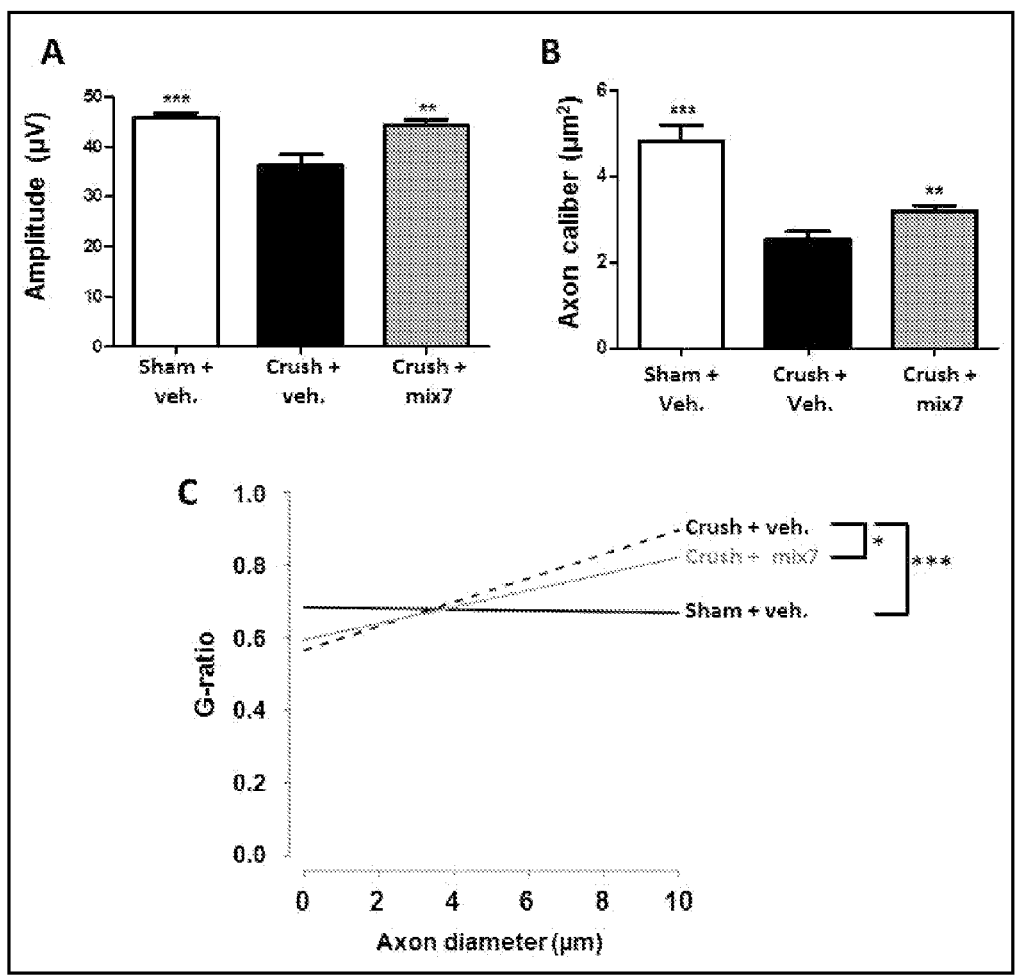

Electrophysiological recordings were performed 30 days after the crush using a Keypoint electromyograph (EMG) (Medtronic, France). Mice were anaesthetized by 2.5-3% isoflurane and subcutaneous monopolar needle electrodes were used for both stimulation and recording. Supramaximal (12.8 mA) square waves pulses of 0.2 ms were delivered to stimulate the sciatic nerve (proximal side of crush). The right sciatic nerve (ipsilateral) was stimulated with single pulse applied at the sciatic notch. CMAP was recorded by needle electrodes placed at the gastrocnemius muscle. The amplitude ($\mu V$) of the action potential, which reflects the level of denervation and of reinnervation of muscles, was determined (FIG. 15, panel A).

3. Morphometric Analyses

Forty two days after the crush, the tibial nerve was taken out of 6 mice per group (described above) to perform a morphometric analysis as follows: composite image of the entire nerve section of each sample was obtained using an optical microscope (Nikon optiphot-2) equipped with a digital camera (Nikon DS-Fil). Morphometric analyses were performed with digital images using Image-Pro Plus software (Media Cybernetics Inc., USA), which computes the axonal and myelin pixel sizes after individualization of each myelinated fibre via the grey level of toluidine blue-stained myelin sheath. This allowed the determination of axon calibre (FIG. 15, panel B) and the G-ratio which is the ratio between the inner axonal diameter and the outer diameter of the neuronal fiber (i.e. axon+myelin thickness). The balance between the g-ratio and the axon diameter is indicative of the myelination of neurons (FIG. 15, panel C).

4. Results

A significant improvement of CMAP amplitude (around 84%, FIG. 15, panel A) is noticed when compared to the crushed non-treated animals and this as early as 3 weeks of treatment, thereby showing an accelerated functional restoration of the nerves. Morphometric analysis also shows a significant increase of axon calibre (around 30% after 6 weeks of treatment, FIG. 15, panel B), which the signature of nerve growth promotion. Such an improvement in morphological and electrophysiological features of the nerves characterizes a nerve regeneration which is triggered by mix7.

A normalisation of axon myelination is also observed upon treatment with composition of the invention. A normal myelination state is characterized by an almost uniform myelination of axons, which is characterized by a constant G-ratio regardless the diameter of the axon (FIG. 15, panel C, black horizontal line). Nerve injury by a crush as mentioned above results in a significant disturbance of myelination of axons. Forty two days from a crush, an hypermyelination of small axons (low diameter) together with an hypomyelination of large axons are noticed when compared to the sham animals; which results by a positively correlation between G-ratio and axon diameter (FIG. 15, panel C, black dotted line with a positive slope).

Upon treatment with Mix7, a normalization of axon myelinisation is observed 42 days from the crush (FIG. 15, panel C, grey line) which is illustrated by a distribution of G-ratio according to the axon diameter showing an intermediate slope when compared to the sham animals (black line) and to the non-treated crushed-animals (dotted black line).

These results underline the high potential of the compositions of the invention in improving and/or accelerating recovery from a neuronal insult, by acting on the myelin sheaths (for the myelinated neurons) or the electrophysiological functions and/or the integrity of the axons.

Hence, compositions of the invention are particularly efficient in correcting nerve injuries through the promotion of nerve regeneration.

G. In Vivo Effect of Composition of the Invention Assessed in a Clinical Trial Positive effects of compositions of the invention on CMT disease were confirmed in clinical trials. The trial was a one year, double-blind, randomized, placebo-controlled phase-2 study. The primary objective of the study was to evaluate the safety and tolerability of Mix7 in patient suffering from CMT disease. The secondary objectives aimed at an exploratory analysis of Mix7 efficacy to be used for organization of further studies in patients.

1. Methods

Patients, Randomization and Blinding

Potentially eligible subjects were evaluated at screening visits that included notably confirmation of CMT1A genotyping, recording of the Charcot-Marie-Tooth Neuropathy Score (CMTNS, Shy et al., 2005), Overall Neuropathy Limitations Scale (ONLS, Graham et al., 2006) to ascertain CMT1A diagnosis.

Female and male patients, aged 18-65 years, diagnosed with CMT1A according to clinical examination and confirmation by genotyping, weakness in at least foot dorsiflexion, and a Charcot Marie Tooth neuropathy score (CMTNS) of <20 were randomly assigned in a 1:1:1:1 ratio to receive daily for one year Placebo or Mix7 ((RS)-baclofen: 6 mg/day, naltrexone: 0.7 mg/day, D-sorbitol: 210 mg/day). A randomization block scheme was used, stratified by study centre. All investigators and patients were unaware of the treatment allocation.

Safety, Tolerability, Compliance

Safety of mix during the study including the 1-month follow-up visit after the last day of Mix7 administration was monitored based on adverse events reports from patients and laboratory tests. Compliance was monitored at each visit (1, 3, 9 and 12 months) by returned empty bottle count and volume measurement. Mean (SD) duration of exposure overall was 11.69 (1.53) months and was similar among the groups, and mean (SD) compliance with study drug was 97.3 (9.41) %.

Electrophysiology Assays

Nerve conduction studies were performed using standard techniques at skin temperature of 32° C. Both sensory and motor functions were assayed on median and ulnar nerves of the non-dominant upper limb.

For motor parameters (amplitude of Compound Muscle Action Potential (CMAP, in millivolt) and distal motor latency (DML, in millisecond)), the median nerve was stimulated at the wrist, antecubital fossa and responses were recorded over the abductor pollicis brevis. The ulnar nerve was stimulated at the wrist and below the elbow, and responses were recorded over the abductor digiti minimi.

For sensory parameters (amplitude of Sensory Nerve Action Potential (SNAP, in millivolt) and Sensory Conduction Velocity (SCV, in meter per second), an antidromic method was used and nerves were stimulated by ring electrodes placed at the wrist. For the median nerve, the active electrode was placed at the basis of the second digit and the reference electrode between the fourth and the fifth metacarpals of the second digit. For the ulnar nerve, the active electrode was placed at the basis of the fifth digit and the reference electrode between the fourth and the fifth metacarpals of the fifth digit.

The Charcot-Marie-Tooth Neuropathy Score (CMTNS)

CMTNS was proposed and validated by Shy et at (2005) to provide a single and reliable measure of CMT severity[22]. It is currently the sole CMT-specific outcome measure (although not specific to CMT1A). CMTNS is a 36-point scale based on 9 items comprising 5 of impairment (sensory symptoms, pin sensibility, vibration, strength arms and legs), 2 of activity limitations (motor symptoms arms and legs) and 2 of Electrophysiology (amplitudes of ulnar CMAP and SNAP). Higher scores indicate worsening function, and the score categorizes disability as mild (0-10), moderate (11-20) and severe (21-36).

The Overall Neuropathy Limitations Scale (ONLS)

ONLS was derived and improved from the ODSS by Graham and Hughes (2006) to measure limitations in the everyday activities of the upper limbs (rated on 5 points) and the lower limbs (rated on 7 points)[23]. The total score goes from 0 (=no disability) to 12 (=maximum disability). Although the functioning of patients with peripheral neuropathy may be influenced by other factors in addition to their physical capacity, ONLS measures the perceived ability of the patient to move and fulfil normal life, and thus is expected to be associated with Quality of Life.

Statistical Analyses

Statistical analyses were performed with R version 3.0.1 or later (http://cran.r-project.org). Data distribution and within-group variation were preliminary assessed in order to guide the methodological choices (Markowski et al., 1990; Sawilowski & Blair; Vickers, 2005). Assuming data as Missing At Random (MAR, Little & Rubin, 2002), missing data imputation was performed by mixed model approach considered the most appropriate technique for intent to treat longitudinal studies (Chakraborty & Gu, 2009). Results without missing data imputation were compared for sensitivity purposes. Statistical tests were conducted at a 5% significance level.

Population Analysis

All the analyses were conducted on the Full Analysis Set on an intent to treat basis, by including all the randomized patients known to have taken at least one dose of the Mix7 and provided at least one post-baseline efficacy measurement.

Baseline Analysis

Patient characteristics at baseline were descriptively compared between groups, and tested by Fisher's exact test or Analysis Of Variance (ANOVA).

Safety and Tolerability Analysis

Safety and tolerability analyses were based on the reported treatment-emergent adverse events and other safety information (laboratory tests, vital signs, and ECG). The incidence of treatment-emergent adverse events (TEAEs) was descriptively compared between groups and tested by a Fisher's Exact Test.

Efficacy Analysis

Differences between groups were assessed by Analysis of Covariance (ANCOVA) on log-transformed values by adjusting for baseline values. Estimates were provided as mean percentage change over baseline. This analysis was performed independently on the different efficacy outcomes. Due to outcome multiplicity, the significance of the treatment effect on the two main outcomes CMTNS and ONLS was tested by O'Brien's OLS test (O'Brien, 1984; Logan & Tamhane, 2006). This analysis was repeated for the other efficacy outcomes (DML, SCV). Therapy responders were defined as patients who were not deteriorated during the 12-month treatment. The deterioration was evaluated by the percentage of change from baseline averaged over the CMTNS and ONLS. The proportions of responders in each group were compared using a Logistic Regression model. Relative Risks were deduced from Odds-Ratio estimates36. Statistical tests for efficacy analysis were one-tailed. The one-tailed approach was justified on clinical grounds (the unlikely deleterious hypothesis both on efficacy or safety due to extremely low dosages of compounds commercially used on much higher dosages) and statistical efficiency (Lewis et al., 2013; Parikh et al., 2011; De Jager et al., 2010).

2. Results

Safety and Tolerability

Safety and tolerability results of Mix7 were good, since the intake of the treatment did not indicate any influence on the results of vital signs (blood pressure, heart rate and weight), electrocardiogram measurements and laboratory abnormalities (biochemistry and haematology). There was no significant difference in the incidence of treatment-emergent adverse events between placebo and Mix7 group (47% and 31%, respectively). Further, most of the treatment-emergent adverse events were mild and benign.

Efficacy

Treatment with Mix7 leads to an improvement in CMTNS (Table 4, trend, P<0.20) compared to placebo group. ONLS score was also improved in the Mix7 group compared to placebo (Table 4, 14.4% improvement, P<0.05). Indeed, whereas ONLS score was decreased in placebo after one year (FIG. 16, dashed line), it was significantly increased in Mix7 treated group (FIG. 16, solid line). The improvement on patient global condition scores is confirmed when considering the improvement of CMTNS and ONLS in Mix7 group compared to placebo, through the significance of the O'Brien's OLS (P<0.05).

Interestingly, myelin function showed also an improvement in Mix7 group when compared to placebo as assessed by sensory conduction velocity and motor distal latency. Distal Motor Latency (DML) was significantly decreased in Mix7 group when compared to placebo (Table 4, 8%, P<0.05), and Sensory Conduction Velocity (SCV) was significantly increase in Mix7 group when compared to placebo (Table 4, 26.6%, P<0.001). These results are consistent with the impact of Mix7 on Schwann cells functions and do sustain the efficiency of the compositions of the invention in regeneration of the nerve fibres, as observed in the above in vitro and in vivo pre-clinical studies.

TABLE 4

Placebo versus treatment mean percentages of improvement in four tests (mean ± S.D).

| | mean % of improvement | | |
|---|---|---|---|
| | Placebo<br>n = 19 | Mix7<br>n = 19 | P-value |
| CMTNS | 2.6 ± 17.5 | 7.7 ± 18.4 | 0.16 |
| ONLS | −5.3 ± 19.3 | 12.3 ± 28.4 | 0.043 |
| DML (ms) | 0.4 ± 8.8 | 8.4 ± 21.7 | 0.038 |
| SCV (m/s) | 3.4 ± 11.0 | 30.5 ± 10.0 | 0.00037 |

Finally, the proportion of therapy responders, defined as patients not deteriorated during the 12-months treatment, was significantly higher in Mix7 group (79%, Relative Risk 1.66, P=0.01).

TABLE 5

Placebo versus Mix7 group responders. The number of patients is followed by the corresponding percentage into brackets. Relative Risk is followed by the interval range.

| | Placebo | Mix7 | Mix7 versus Placebo | |
|---|---|---|---|---|
| | n = 19 | n = 19 | Relative Risk | P-value |
| Responders | 10 (52%) | 15 (79%) | 1.5 (1.03; 1.77) | 0.047 |

By considering the baseline characteristics (recorded at the beginning of the study) between responders and non-responders, it appeared that the responders were globally less severely affected by the disease. Not only useful in slowing down the progression of the disease in patients at an advanced stage of the disease, the compositions of the invention could be expected to have a particular interest for slowing down the disease in patients weakly affected or at an early stage of the disease such as children.

BIBLIOGRAPHY

Amici S A, Dunn W A Jr, Murphy A J, Adams N C, Gale N W, Valenzuela D M, Yancopoulos G D, Notterpek L. Peripheral myelin protein 22 is in complex with alpha6beta4 integrin, and its absence alters the Schwann cell basal lamina. J Neurosci. 2006; 26(4):1179-1189.

Amici S A, Dunn W A Jr, Notterpek L. Developmental abnormalities in the nerves of peripheral myelin protein 22-deficient mice. J Neurosci Res. 2007; 85(2): 238-249.

Atanasoski S, Scherer S S, Nave K-A, Suter U. Proliferation of Schwann Cells and Regulation of Cyclin D1 Expression in an Animal Model of Charcot-Marie-Tooth Disease Type 1A. J Neurosci Res. 2002; 67(4):443-449.

Basta-Kaim A, Budziszewska B, Jaworska-Feil L, Tetich M, Leśkiewicz M, Kubera M, Lasoń W. Chlorpromazine inhibits the glucocorticoid receptor-mediated gene transcription in a calcium-dependent manner. Neuropharmacology 2002; 43(6):1035-1043.

Batty I H, Fleming I N, Downes C P. Muscarinic-receptor-mediated inhibition of insulin-like growth factor-1 receptor-stimulated phosphoinositide 3-kinase signalling in 1321N1 astrocytoma cells. Biochem J. 2004; 379(Pt 3):641-651.

Bogoyevitch M A, Ketterman A J, Sugden P H. Cellular stresses differentially activate c-Jun N-terminal protein kinases and extracellular signal-regulated protein kinases in cultured ventricular myocytes. J Biol Chem. 1995; 270 (50):29710-29717.

Brancolini C, Marzinotto S, Edomi P, Agostoni E, Fiorentini C, Müller H W, Schneider C. Rho-dependent regulation of cell spreading by the tetraspan membrane protein Gas3/PMP22. Mol. Biol. Cell 1999; 10: 2441-2459.

Castellone M D, Teramoto H, Gutkind J S. Cyclooxygenase-2 and Colorectal Cancer Chemoprevention: The β-Catenin Connection. Cancer Res. 2006; 66(23):11085-11088.

Chakraborty H. & Gu H. A mixed model approach for intent-to-treat analysis in longitudinal clinical trials with missing values. RTI Press Publ. MR-0009-09, (2009).

Chen X R, Besson V C, Palmier B, Garcia Y, Plotkine M, Marchand-Leroux C. Neurological recovery-promoting, anti-inflammatory, and anti-oxidative effects afforded by fenofibrate, a PPAR alpha agonist, in traumatic brain injury. J Neurotrauma 2007; 24 (7): 1119-1131.

Chies R, Nobbio L, Edomi P, Schenone A, Schneider C, Brancolini C. Alterations in the Arf6-regulated plasma membrane endosomal recycling pathway in cells overexpressing the tetraspan protein Gas3/PMP22. J Cell Sci. 2003; 116(Pt 6): 987-999.

Constable A L, Armati P J. DMSO induction of the leukotriene LTC4 by Lewis rat Schwann cells. J Neurol Sci 1999; 162(2): 120-126.

Cosgaya J. M., Chan J. R., Shooter E. M. The Neurotrophin Receptor p75NTR as a Positive Modulator of Myelination. Science. 2002; 298; 1245-1248.

De Jager J, Kooy A, Lehert P, Wulffelé M G, van der Kolk J, Bets D, Verburg J, Donker A J, Stehouwer C D. Long term treatment with metformin in patients with type 2 diabetes and risk of vitamin B-12 deficiency: randomised placebo controlled trial. BMJ 340, c2181 (2010).

Devaux J J, Scherer S S. Altered ion channels in an animal model of Charcot-Marie-Tooth disease type IA. J Neurosci. 2005; 25(6): 1470-1480.

Diep Q N, Benkirane K, Amiri F, Cohn J S, Endemann D, Schiffrin E L. PPAR alpha activator fenofibrate inhibits myocardial inflammation and fibrosis in angiotensin II-infused rats. J Mol Cell Cardiol. 2004; 36 (2): 295-304.

Dracheva S, Davis K L, Chin B, Woo D A, Schmeidler J, Haroutunian V. Myelin-associated mRNA and protein expression deficits in the anterior cingulate cortex and hippocampus in elderly schizophrenia patients. Neurobiol Dis. 2006 March; 21(3):531-540.

D'Urso D, Ehrhardt P, Müller H W. Peripheral myelin protein 22 and protein zero: a novel association in peripheral nervous system myelin. J Neurosci. 1999; 19(9):3396-3403.

Fortun J, Dunn W A Jr, Joy S, Li J, Notterpek L. Emerging role for autophagy in the removal of aggresomes in Schwann cells. J Neurosci. 2003; 23(33): 10672-10680.

Fortun J, Li J, Go J, Fenstermaker A, Fletcher B S, Notterpek L. Impaired proteasome activity and accumulation of ubiquitinated substrates in a hereditary neuropathy model. J Neurochem 2005; 92:1531-1541.

Fortun J, Go J C, Li J, Amici S A, Dunn W A Jr, Notterpek L. Alterations in degradative pathways and protein aggregation in a neuropathy model based on PMP22 overexpression. Neurobiol Dis. 2006; 22(1):153-164.

Fortun J, Verrier J D, Go J C, Madorsky I, Dunn W A, Notterpek L. The formation of peripheral myelin protein 22 aggregates is hindered by the enhancement of autophagy and expression of cytoplasmic chaperones. Neurobiol Dis. 2007; 25(2): 252-265.

Gale K, Kerasidis H, Wrathall J R. Spinal cord contusion in the rat: behavioral analysis of functional neurologic impairment. Exp Neurol. 1985 April; 88(1):123-34.

Galvez A S, Ulloa J A, Chiong M, Criollo A, Eisner V, Barros L F, Lavandero S. Aldose reductase induced by hyperosmotic stress mediates cardiomyocyte apoptosis: differential effects of sorbitol and mannitol. J Biol Chem. 2003; 278(40):38484-38494.

Graham R C & Hughes, R A. A modified peripheral neuropathy scale: the Overall Neuropathy Limitations Scale. J. Neurol. Neurosurg. Psychiatry 77, 973-976 (2006).

Groyer G, Eychenne B, Girard C, Rajkowski K, Schumacher M, Cadepond F. Expression and functional state of the corticosteroid receptors and 11 beta-hydroxysteroid dehydrogenase type 2 in Schwann cells. Endocrinology. 2006; 147(9):4339-4350.

Howland D S, Liu J, She Y, Goad B, Maragakis N J, Kim B, Erickson J, Kulik J, DeVito L, Psaltis G, DeGennaro L J, Cleveland D W, Rothstein J D. Focal loss of the glutamate transporter EAAT2 in a transgenic rat model of SOD1 mutant-mediated amyotrophic lateral sclerosis (ALS). Proc Natl Acad Sci USA. 2002 Feb. 5; 99(3):1604-9. Epub 2002 Jan. 29.

Kantamneni S, Corrêa S A, Hodgkinson G K, Meyer G, Vinh N N, Henley J M, Nishimune A. GISP: a novel brain-specific protein that promotes surface expression and function of GABA(B) receptors. J Neurochem. 2007; 100(4): 1003-17.

Kirshblum S C, Burns S P, Biering-Sorensen F, Donovan W, Graves D E, Jha A, Johansen M, Jones L, Krassioukov A, Mulcahey M J, Schmidt-Read M, Waring W. The Journal of Spinal Cord Medicine 2011; 34 (6):535-46.

Khajavi M, Shiga K, Wiszniewski W, He F, Shaw C A, Yan J, Wensel T G, Snipes G J, Lupski J R. Oral curcumin mitigates the clinical and neuropathologic phenotype of the Trembler-J mouse: a potential therapy for inherited neuropathy. Am J Hum Genet. 2007; 81(3): 438-453.

Kobsar I, Hasenpusch-Theil K, Wessig C, Müller H W, Martini R. Evidence for Macrophage-Mediated Myelin Disruption in an Animal Model for Charcot-Marie-Tooth Neuropathy Type 1A. J. Neurosci Res 2005; 81:857-864.

Lange C A, Shen T et al. Phosphorylation of human progesterone receptors at serine-294 by mitogen-activated protein kinase signals their degradation by the 26S proteasome. PNAS USA. 2000; 97: 1032-1037.

Le-Niculescu H, Kurian S M, Yehyawi N, Dike C, Patel S D, Edenberg H J, Tsuang M T, Salomon D R, Nurnberger J I Jr, Niculescu A B. Identifying blood biomarkers for mood disorders using convergent functional genomics. Mol Psychiatry. 2008 Feb. 26. [Epub ahead of print].

Lewis R A, McDermott M P, Herrmann D N, Hoke A, Clawson L L, Siskind C, Feely S M, Miller L J, Barohn R J, Smith P, Luebbe E, Wu X, Shy M E; Muscle Study Group. High-Dosage Ascorbic Acid Treatment in Charcot-Marie-Tooth Disease Type 1A: Results of a Randomized, Double-Masked, Controlled Trial. JAMA Neurol. 70, 981-7 (2013).

Li W W, Le Goascogne C, Ramaugé M, Schumacher M, Pierre M, Courtin F. Induction of type 3 iodothyronine deiodinase by nerve injury in the rat peripheral nervous system. Endocrinology. 2001; 142(12):5190-5197.

Little R J A & Rubin D B. Statistical Analysis with Missing Data. 408 (Wiley-Interscience, 2002).

Logan B R & Tamhane A C. On O'Brien's OLS and GLS tests for multiple endpoints. Lect. Notes-Monograph Ser. 47, 76-88 (2006).

Lupski J R, Wise C A, Kuwano A, Pentao L, Parke J T, Glaze D G, Ledbetter D H, Greenberg F, Patel P I. Gene dosage is a mechanism for Charcot-Marie-Tooth disease type 1A. Nat Genet. 1992; 1(1): 29-33.

Markowski C A & Markowski E P. Conditions for the Effectiveness of a Preliminary Test of Variance. Am. Stat. 44, 322-326 (1990).

Matsumoto A, Okada Y, Nakamichi M, Nakamura M, Toyama Y, Sobue G, Nagai M, Aoki M, Itoyama Y, Okano H. Disease progression of human SOD1 (G93A) transgenic ALS model rats. J Neurosci Res. 2006 January; 83(1):119-33.

Mäurer M, Kobsar I, Berghoff M, Schmid C D, Carenini S, Martini R. Role of immune cells in animal models for inherited neuropathies: facts and visions. J Anat. 2002; 200(4): 405-414.

Melcangi R C, Cavarretta I T, Ballabio M, Leonelli E, Schenone A, Azcoitia I, Miguel Garcia-Segura L, Magnaghi V. Peripheral nerves: a target for the action of neuroactive steroids. Brain Res Rev. 2005; 48(2): 328-338.

Mercier G, Turque N, Schumacher M. Rapid effects of triiodothyronine on immediate-early gene expression in Schwann cells. Glia. 2001; 35(2):81-89.

Meyer Zu Horste G., Nave K-A. Animal models of inherited neuropathies. Curr. Opin. Neurol. 2006; 19(5): 464-473.

Meyer zu Horste G, Prukop T, Liebetanz D, Mobius W, Nave K A, Sereda M W. Antiprogesterone therapy uncouples axonal loss from demyelination in a transgenic rat model of CMT1A neuropathy. Ann Neurol. 2007; 61 (1): 61-72.

Miller A L, Garza A S, Johnson B H, Thompson E B. Pathway interactions between MAPKs, mTOR, PKA, and the glucocorticoid receptor in lymphoid cells. Cancer Cell Int. 2007; 28:7:3.

Muja N, Blackman S C, Le Breton G C, DeVries G H. Identification and functional characterization of thromboxane A2 receptors in Schwann cells. J Neurochem. 2001; 78(3): 446-456.

Muller D L, Unterwald E M. In vivo Regulation of Extracellular Signal-Regulated Protein Kinase (ERK) and Protein Kinase B (Akt) Phosphorylation by Acute and Chronic Morphine. JPET 2004; 310:774-782.

Nambu H, Kubo E, Takamura Y, Tsuzuki S, Tamura M, Akagi Y. Attenuation of aldose reductase gene suppresses high-glucose-induced apoptosis and oxidative stress in rat lens epithelial cells. Diabetes Res Clin Pract. 2008; 82(1):18-24.

Nave K A, Sereda M W, Ehrenreich H. Mechanisms of disease: inherited demyelinating neuropathies—from basic to clinical research. Nat Clin Pract Neurol. 2007; 3(8): 453-464.

Niemann S., Sereda M. W., Rossner M., Stewart H., Suter U., Meinck H. M., Griffiths I. R., Nave K-A. The "CMT rat": peripheral neuropathy and dysmyelination caused by transgenic overexpression of PMP22. Ann. N.-Y. Acad. Sci. 1999; 883:254-261.

Notterpek L, Shooter E M, Snipes G J. Upregulation of the endosomal-lysosomal pathway in the trembler-J neuropathy. J Neurosci. 1997; 17(11): 4190-4200.

O'Brien P. Procedures for Comparing Samples with Multiple Endpoints. Biometrics 40, 1079-1087 (1984).

Obrietan K, van den Pol A N. GABAB receptor-mediated inhibition of GABAA receptor calcium elevations in developing hypothalamic neurons. J Neurophysiol. 1998; 79(3): 1360-1370.

Ogata T, Iijima S, Hoshikawa S, Miura T, Yamamoto S, Oda H, Nakamura K, Tanaka S Opposing extracellular signal-regulated kinase and Akt pathways control Schwann cell myelination. J Neurosci. 2004; 24(30):6724-6732.

Ohsawa Y, Murakami T, Miyazaki Y, Shirabe T, Sunada Y. Peripheral myelin protein 22 is expressed in human central nervous system. J Neurol Sci. 2006; 247(1):11-15.

Parikh P M, Vaid A, Advani S H, Digumarti R, Madhavan J, Nag S, Bapna A, Sekhon J S, Patil S, Ismail P M, Wang Y, Varadhachary A, Zhu J, Malik R. Randomized, double-blind, placebo-controlled phase II study of single-agent oral talactoferrin in patients with locally advanced or metastatic non-small-cell lung cancer that progressed after chemotherapy. J. Clin. Oncol. 29, 4129-36 (2011).

Passage E, Norreel J C, Noack-Fraissignes P, Sanguedolce V, Pizant J, Thirion X, Robaglia-Schlupp A, Pellissier J F, Fontes M. Ascorbic acid treatment corrects the phenotype of a mouse model of Charcot-Marie-Tooth disease. Nature Med. 2004; 10(4): 396-401.

Perea J, Robertson A, Tolmachova T, Muddle J, King R H, Ponsford S, Thomas P K, Huxley C. Induced myelination and demyelination in a conditional mouse model of Charcot-Marie-Tooth disease type 1A. Hum Mol Genet. 2001; 10(10):1007-1018.

Rangaraju S, Madorsky I, Pileggi J G, Kamal A, Notterpek L. Pharmacological induction of the heat shock response improves myelination in a neuropathic model. Neurobiology of Disease. 2008; 32(105-115).

Roa B B, Garcia C A, Suter U, Kulpa D A, Wise C A, Mueller J, Welcher A A, Snipes G J, Shooter E M, Patel P I, Lupski J R. Charcot-Marie-Tooth disease type 1A. Association with a spontaneous point mutation in the PMP22 gene. N Engl J Med. 1993; 329(2): 96-101.

Robaglia-Schlupp A, Pizant J, Norreel J C, Passage E, Saberan-Djoneidi D, Ansaldi J L, Vinay L, Figarella-Branger D, Levy N, Clarac F, Cau P, Pellissier J F, Fontes M. PMP22 overexpression causes dysmyelination in mice. Brain 2002; 125(Pt 10): 2213-2221.

Robert F, Guennoun R, Désarnaud F, Do-Thi A, Benmessahel Y, Baulieu E E, Schumacher M. Synthesis of progesterone in Schwann cells: regulation by sensory neurons. Eur J Neurosci. 2001; 13(5): 916-924.

Roux K J, Amici S A, Notterpek L. The temporospatial expression of peripheral myelin protein 22 at the developing blood-nerve and blood-brain barriers. J Comp Neurol. 2004; 474(4):578-588.

Sancho S, Young P, Suter U. Regulation of Schwann cell proliferation and apoptosis in PMP22-deficient mice and mouse models of Charcot-Marie-Tooth disease type 1A. Brain 2001; 124(Pt 11): 2177-2187.

Sawilowsky S S. & Blair R C. A more realistic look at the robustness and Type II error properties of the t test to departures from population normality. Psychological Bulletin 1992; 111(2): 352-360.

Schumacher M, Guennoun R, Mercier G, Désarnaud F, Lacor P, Bénavides J, Ferzaz B, Robert F, Baulieu E E. Progesterone synthesis and myelin formation in peripheral nerves. Brain Res Rev. 2001; 37(1-3): 343-359.

Sereda M W, Meyer zu Horste G, Suter U, et al. Therapeutic administration of progesterone antagonist in a model of Charcot-Marie-Tooth disease (CMT-1A). Nat Med 2003; 9: 1533-1537.

Sereda M W, Nave K A. Animal models of Charcot-Marie-Tooth disease type 1A (CMT1A). Neuromol Med 2006; 8: 205-215.

Shy M E, Blake J, Krajewski K, Fuerst D R, Laura M, Hahn A F, Li J, Lewis R A, Reilly M. Reliability and validity of the CMT neuropathy score as a measure of disability. Neurology 64, 1209-1214 (2005).

Stirnweiss J, Valkova C, Ziesché E, Drube S, Liebmann C. Muscarinic M2 receptors mediate transactivation of EGF receptor through Fyn kinase and without matrix metalloproteases. Cell Signal. 2006; 18(8):1338-1349.

Suter U, Scherer S S. Disease mechanisms in inherited neuropathies. Nat. Rev. Neurosci. 2003; 4: 714-726.

Suter U, Welcher A A, Ozcelik T, Snipes G J, Kosaras B, Francke U, Billings-Gagliardi S, Sidman R L, Shooter E M. Trembler mouse carries a point mutation in a myelin gene. Nature. 1992; 356(6366): 241-244.

Thonhoff J R, Jordan P M, Karam J R, Bassett B L, Wu P. Identification of early disease progression in an ALS rat model. Neurosci Lett. 2007 Mar. 30; 415(3):264-8. Epub 2007 Jan. 14.

Thomas P K, Marques W Jr, Davis M B, Sweeney M G, King R H, Bradley J L, Muddle J R, Tyson J, Malcolm S, Harding A E. The phenotypic manifestations of chromosome 17p11.2 duplication. Brain 1997; 120 (Pt 3): 465-478.

Tobler A R, Liu N, Mueller L, Shooter E M. Differential aggregation of the Trembler and Trembler J mutants of peripheral myelin protein 22. PNAS USA. 2002; 99(1): 483-488.

Tu H, Rondard P, Xu C, Bertaso F, Cao F, Zhang X, Pin J P, Liu J. Dominant role of GABAB2 and Gbetagamma for GABAB receptor-mediated-ERK1/2/CREB pathway in cerebellar neurons. Cell Signal. 2007; 19(9):1996-2002.

Uht R M, Anderson C M, Webb P, Kushner P J. Transcriptional activities of estrogen and glucocorticoid receptors are functionally integrated at the AP-1 response element. Endocrinology. 1997 July; 138(7):2900-2908.

Ulzheimer J C, Peles E, Levinson S R, Martini R. Altered expression of ion channel isoforms at the node of Ranvier in P0-deficient myelin mutants. Mol Cell Neurosci. 2004; 25(1): 83-94.

Vallat J M, Sindou P, Preux P M, Tabaraud F, Milor A M, Couratier P, LeGuern E, Brice A. Ultrastructural PMP22 expression in inherited demyelinating neuropathies Ann Neurol. 1996; 39(6): 813-817.

Vickers A J. Parametric versus non-parametric statistics in the analysis of randomized trials with non-normally distributed data. BMC Med. Res. Methodol. 5, 35 (2005).

Walter I B. Nuclear triiodothyronine receptor expression is regulated by axon-Schwann cell contact. Neuroreport. 1993; 5(2):137-140.

Walter I B, Deruaz J P, de Tribolet N. Differential expression of triiodothyronine receptors in schwannoma and neurofibroma: role of Schwann cell-axon interaction. Acta Neuropathol (Berl). 1995; 90(2):142-149.

Welch W J, Brown C R. Influence of molecular and chemical chaperones on protein folding. Cell Stress Chaperones. 1996; 1(2): 109-115.

Woodhams P L, MacDonald R E, Collins S D, Chessell I P, Day N C. Localisation and modulation of prostanoid receptors EP1 and EP4 in the rat chronic constriction injury model of neuropathic pain. Eur J Pain. 2007; 11(6):605-613.

We claim:

1. A method of treating Charcot-Marie-Tooth disease or a neuropathy, comprising administering to a subject in need thereof a composition comprising an effective amount of at least baclofen, D-sorbitol and naltrexone, or pharmaceutically acceptable salts thereof, wherein baclofen, D-sorbitol and naltrexone are in a relative weight ratio of 8.6/300/1.

2. The method of claim 1, wherein the composition further comprises a pharmaceutically suitable excipient or carrier.

3. The method of claim 1, wherein the composition is formulated with a drug eluting polymer, a biomolecule, a micelle or liposome-forming lipids or oil in water emulsions, or pegylated or solid nanoparticles or microparticles for oral or parenteral or intrathecal administration.

4. The method of claim 1, wherein the neuropathy is selected from idiopathic neuropathies, diabetic neuropathy, toxic neuropathies, neuropathies induced by drug treatments, neuropathies provoked by HIV, neuropathies provoked by radiation, neuropathies provoked by heavy metals, neuropathies provoked by vitamin deficiency states, or traumatic neuropathies.

5. The method of claim 4, wherein the traumatic neuropathies arise from brain injury, spinal cord injury, or peripheral nerves injuries.

6. A method of improving nerve regeneration in a subject suffering from Charcot-Marie-Tooth disease, amyotrophic lateral sclerosis, or a neuropathy selected from an idiopathic neuropathy, diabetic neuropathy, a toxic neuropathy, a neuropathy induced by drug treatment, a neuropathy provoked by HIV, a neuropathy provoked by radiation, a neuropathy provoked by heavy metals, a neuropathy provoked by vitamin deficiency states, or a traumatic neuropathy, said method comprising administering to said subject an amount of a composition effective to improve nerve regeneration in said subject, said composition comprising baclofen, D-sorbitol and naltrexone or pharmaceutically acceptable salts thereof, wherein baclofen, D-sorbitol and naltrexone are in a relative weight ratio of 8.6/300/1.

7. The method of claim 6, wherein the composition further comprises a pharmaceutically suitable excipient or carrier.

8. The method of claim 6, wherein the composition is formulated with a drug eluting polymer, a biomolecule, a micelle or liposome-forming lipids or oil in water emulsions, or pegylated or solid nanoparticles or microparticles for oral or parenteral or intrathecal administration.

9. The method of claim 6, wherein improving nerve regeneration comprises improving or accelerating recovery.

10. The method of claim 6, wherein improving nerve regeneration comprises improving nerve myelination or restoring, at least partially, axon morphology or electrophysiological functions.

11. The method of claim 6, wherein the traumatic neuropathy arises from brain injury, spinal cord injury, or peripheral nerves injuries.

* * * * *

SEQUENCE LISTING

```
<160> NUMBER OF SEQ ID NOS: 14

<210> SEQ ID NO 1
<211> LENGTH: 17
<212> TYPE: DNA
<213> ORGANISM: artificial sequence
```

```
<220> FEATURE:
<223> OTHER INFORMATION: forward primer_rat PMP22

<400> SEQUENCE: 1
ggaaacgcga atgaggc                                                  17

<210> SEQ ID NO 2
<211> LENGTH: 19
<212> TYPE: DNA
<213> ORGANISM: Artificial sequence
<220> FEATURE:
<223> OTHER INFORMATION: reverse primer_rat PMP22

<400> SEQUENCE: 2
gttctgtttg gtttggctt                                                19

<210> SEQ ID NO 3
<211> LENGTH: 17
<212> TYPE: DNA
<213> ORGANISM: Artificial sequence
<220> FEATURE:
<223> OTHER INFORMATION: forward primer_RPL13A

<400> SEQUENCE: 3
ctgccctcaa ggttgtg                                                  17

<210> SEQ ID NO 4
<211> LENGTH: 21
<212> TYPE: DNA
<213> ORGANISM: Artificial sequence
<220> FEATURE:
<223> OTHER INFORMATION: reverse primer_RPL13A

<400> SEQUENCE: 4
cttcttcttc cggtaatgga t                                             21

<210> SEQ ID NO 5
<211> LENGTH: 22
<212> TYPE: DNA
<213> ORGANISM: Artificial sequence
<220> FEATURE:
<223> OTHER INFORMATION: forward primer_Pmp22-FL

<400> SEQUENCE: 5
gctctgagcg tgcatagggt ac                                            22

<210> SEQ ID NO 6
<211> LENGTH: 19
<212> TYPE: DNA
<213> ORGANISM: Artificial sequence
<220> FEATURE:
<223> OTHER INFORMATION: forward primer_ Rpl13A-FL

<400> SEQUENCE: 6
tcgggtggaa gtaccagcc                                                19

<210> SEQ ID NO 7
<211> LENGTH: 25
<212> TYPE: DNA
<213> ORGANISM: Artificial sequence
<220> FEATURE:
<223> OTHER INFORMATION: reverse primer_Pmp22-red

<400> SEQUENCE: 7
agggagggag gaaggaaacc agaaa                                         25
```

<210> SEQ ID NO 8
<211> LENGTH: 28
<212> TYPE: DNA
<213> ORGANISM: Artificial sequence
<220> FEATURE:
<223> OTHER INFORMATION: reverse primer_Rpl13A-red

<400> SEQUENCE: 8
tgacagctac tctggaggag aaacggaa                                      28

<210> SEQ ID NO 9
<211> LENGTH: 19
<212> TYPE: DNA
<213> ORGANISM: artificial sequence
<220> FEATURE:
<223> OTHER INFORMATION: SRY - Forward

<400> SEQUENCE: 9
gagagaggca caagttggc                                                19

<210> SEQ ID NO 10
<211> LENGTH: 19
<212> TYPE: DNA
<213> ORGANISM: artificial sequence
<220> FEATURE:
<223> OTHER INFORMATION: SRY - reverse

<400> SEQUENCE: 10
gcctcctgga aaagggcc                                                 19

<210> SEQ ID NO 11
<211> LENGTH: 19
<212> TYPE: DNA
<213> ORGANISM: artificial sequence
<220> FEATURE:
<223> OTHER INFORMATION: PMP22-forward

<400> SEQUENCE: 11
tgtaccacat ccgccttgg                                                19

<210> SEQ ID NO 12
<211> LENGTH: 22
<212> TYPE: DNA
<213> ORGANISM: artificial sequence
<220> FEATURE:
<223> OTHER INFORMATION: PMP22 - reverse

<400> SEQUENCE: 12
gagctggcag aagaacagga ac                                            22

<210> SEQ ID NO 13
<211> LENGTH: 20
<212> TYPE: DNA
<213> ORGANISM: artificial sequence
<220> FEATURE:
<223> OTHER INFORMATION: MPZ - forward

<400> SEQUENCE: 13
tgttgctgct gttgctcttc                                               20

<210> SEQ ID NO 14
<211> LENGTH: 21
<212> TYPE: DNA
<213> ORGANISM: artificial sequence
<220> FEATURE:
<223> OTHER INFORMATION: MPZ - reverse

```
<400> SEQUENCE: 14
ttgtgaaatt tcccttctc c                                           21
```